(12) United States Patent
Glue et al.

(10) Patent No.: US 12,350,378 B2
(45) Date of Patent: *Jul. 8, 2025

(54) EXTENDED RELEASE PHARMACEUTICAL FORMULATION AND METHODS OF TREATMENT

(71) Applicant: DOUGLAS PHARMACEUTICALS LTD., Auckland (NZ)

(72) Inventors: Paul William Glue, Dunedin (NZ); Natalie June Medlicott, Dunedin (NZ); Peter William Surman, Auckland (NZ)

(73) Assignee: DOUGLAS PHARMACETICALS LTD, Auckland (NZ)

( * ) Notice: Subject to any disclaimer, the term of this patent is extended or adjusted under 35 U.S.C. 154(b) by 308 days.

This patent is subject to a terminal disclaimer.

(21) Appl. No.: 17/851,451

(22) Filed: Jun. 28, 2022

(65) Prior Publication Data

US 2022/0354798 A1 Nov. 10, 2022

Related U.S. Application Data

(63) Continuation of application No. 16/754,389, filed as application No. PCT/IB2018/057851 on Oct. 10, 2018, now Pat. No. 11,471,415, which is a continuation-in-part of application No. 15/728,695, filed on Oct. 10, 2017, now Pat. No. 10,441,544.

(60) Provisional application No. 62/695,966, filed on Jul. 10, 2018.

(51) Int. Cl.
| | |
|---|---|
| A61K 9/28 | (2006.01) |
| A61K 9/00 | (2006.01) |
| A61K 9/20 | (2006.01) |
| A61K 31/135 | (2006.01) |
| A61K 45/06 | (2006.01) |
| A61P 25/22 | (2006.01) |

(52) U.S. Cl.
CPC .......... *A61K 9/2866* (2013.01); *A61K 9/2031* (2013.01); *A61K 9/2813* (2013.01); *A61K 9/2853* (2013.01); *A61K 31/135* (2013.01); *A61P 25/22* (2018.01); *A61K 9/0053* (2013.01); *A61K 45/06* (2013.01)

(58) Field of Classification Search
CPC .. A61K 9/2866; A61K 9/2813; A61K 9/2853; A61K 31/135; A61K 9/2031; A61K 45/06; A61K 9/0053; A61K 9/2095; A61P 25/22

See application file for complete search history.

(56) References Cited

U.S. PATENT DOCUMENTS

| | | | |
|---|---|---|---|
| 6,194,000 B1 | 2/2001 | Smith | |
| 6,280,770 B1 | 8/2001 | Pather et al. | |
| 6,692,771 B2 | 2/2004 | Pather et al. | |
| 6,855,735 B2 | 2/2005 | Friedman | |
| 7,776,314 B2 | 8/2010 | Bartholomaus et al. | |
| 8,114,383 B2 | 2/2012 | Bartholomaus et al. | |
| 8,137,711 B2 | 3/2012 | Wolicki | |
| 8,309,060 B2 | 11/2012 | Bartholomaus et al. | |
| 9,272,037 B2 | 3/2016 | Singh | |
| 9,533,982 B2 | 1/2017 | Conn et al. | |
| 9,650,362 B2 | 5/2017 | Wainer et al. | |
| 9,867,830 B2 | 1/2018 | Wainer et al. | |
| 10,441,544 B2 | 10/2019 | Glue et al. | |
| 10,744,094 B2 | 8/2020 | Glue et al. | |
| 10,869,838 B2 | 12/2020 | Glue et al. | |
| 11,045,424 B2 | 6/2021 | Glue et al. | |
| 11,471,415 B2 | 10/2022 | Glue et al. | |
| 2005/0038062 A1 | 2/2005 | Burns et al. | |
| 2009/0004281 A1 | 1/2009 | Nghiem et al. | |
| 2009/0202634 A1 | 8/2009 | Jans et al. | |
| 2009/0131794 A1 | 10/2009 | Holtman et al. | |
| 2009/0253728 A1 | 10/2009 | Meyerson et al. | |
| 2010/0029665 A1 | 2/2010 | Meyerson et al. | |
| 2013/0088135 A1 | 6/2013 | McCarthy et al. | |
| 2013/0217615 A1 | 8/2013 | Lasser et al. | |
| 2013/0281388 A1 | 10/2013 | Deaver et al. | |
| 2014/0020155 A1 | 2/2014 | Salama | |
| 2014/0050787 A1 | 2/2014 | Tygesen et al. | |
| 2014/0112984 A1 | 4/2014 | Arkenau-Maric et al. | |
| 2015/0057306 A1 | 2/2015 | Fava et al. | |
| 2015/0342947 A1 | 12/2015 | Pollard et al. | |
| 2016/0101069 A1 | 4/2016 | Charney et al. | |
| 2016/0106808 A1 | 4/2016 | Charney et al. | |
| 2016/0199304 A1 | 7/2016 | Nivorozhkin et al. | |
| 2017/0020820 A1 | 1/2017 | Sackler | |
| 2017/0035707 A1 | 2/2017 | Manthei et al. | |
| 2017/0042878 A1 | 2/2017 | Fava et al. | |
| 2017/0355663 A1 | 12/2017 | Nivorozhkin et al. | |
| 2018/0098993 A1 | 4/2018 | Wainer et al. | |

(Continued)

FOREIGN PATENT DOCUMENTS

| | | |
|---|---|---|
| WO | 2009131794 | 10/2009 |
| WO | 2013008135 | 6/2013 |

(Continued)

OTHER PUBLICATIONS

Food and Drug Administration (FDA). FDA label SPRAVATO. https://www.accessdata.fda.gov/drugsatfda_docs/label/2019/211243lbl.pdf. Published 2019.

Glue et al. (2020) "Safety and efficacy of extended release ketamine tablets in patients with treatment-resistant depression and anxiety: open label pilot study" Ther Adv Vaccines 10:1-6 doi:10.1177/2045125320922474.

Kryst et al. (2020) "Efficacy of single and repeated administration of ketamine in unipolar and bipolar depression: a meta-analysis of randomized clinical trials" Pharmacol Reports (0123456789) doi:10.1007/s43440-020-00097-z.

(Continued)

*Primary Examiner* — Aradhana Sasan
(74) *Attorney, Agent, or Firm* — FisherBroyles, LLP; Cara L. Crowley-Weber; Christy G. Rothwell

(57) ABSTRACT

The invention provides an oral extended release formulation for the treatment of treatment-resistant depression, treatment-resistant anxiety, and phobia.

21 Claims, 15 Drawing Sheets

(56) References Cited

U.S. PATENT DOCUMENTS

| | | | |
|---|---|---|---|
| 2018/0153813 | A1 | 6/2018 | Nivorozhkin et al. |
| 2019/0073408 | A1 | 4/2019 | Glue et al. |
| 2019/0105276 | A1 | 4/2019 | Glue et al. |
| 2019/0216740 | A1 | 7/2019 | Glue et al. |
| 2020/0000731 | A1 | 1/2020 | Glue |
| 2020/0323795 | A1 | 10/2020 | Glue et al. |
| 2021/0052517 | A1 | 2/2021 | Glue et al. |
| 2022/0183983 | A1 | 6/2022 | Glue et al. |
| 2022/0354798 | A1 | 11/2022 | Glue et al. |
| 2022/0387355 | A1 | 12/2022 | Glue et al. |

FOREIGN PATENT DOCUMENTS

| | | |
|---|---|---|
| WO | 2013149102 | 10/2013 |
| WO | 2014020155 | 2/2014 |
| WO | 2014169272 | 10/2014 |
| WO | 2015031410 | 3/2015 |
| WO | 2016073653 | 5/2016 |
| WO | 2018234568 | 12/2018 |
| WO | 2019073408 | 4/2019 |

OTHER PUBLICATIONS

Peyrovian et al. (2020) "Registered clinical trials investigating ketamine for psychiatric disorders" J Psychiatr Res 127:1-12 doi:10.1016/j.jpsychires.2020.03.020.

Singh et al. (2016) "A double-blind, randomized, placebo-controlled, dose-frequency study of intravenous ketamine in patients with treatment-resistant depression" Am J Psychiatry 173(8):816-826 doi:10.1176/appi.ajp.2016.16010037.

Adhvaryu et al. (1986) "Genetoxic effects of ketamine on CHO cells" Arch Toxicology 59:124-125.

Amorsa Therapeutics Inc (2014) "Developing a novel treatment for refractory cancer pain" Cancer Cluster Showcase Bio 2014 website www.amorsatx.com.

Anderson et al. (2008) "Evidence-based guidelines for treating depressive disorders with antidepressants: a revision of the 2000 British Association for Psychpharmacology guidelines" A Journal of Psychopharmacology 22(4):343-396.

Amin et al. (2014) "Case report: efficacy and tolerability of ketamine in opioid-refractory cancer pain" J Pain Palliat Care Pharmacother 28(3): 233-242.

Baker et al. (2016) "Ketamine-induced apoptosis in normal human urothelial cells: a direct, N-methyl-d-aspartate receptor-independent pathway characterized by mitochondrial stress" Am J Pathol 186(5): 1267-1277.

Barkan et al. (2014)"A double blind, randomised, placebo controlled trial of oral midazolam plus oral ketamine for sedation of children during laceration repair" Emergency Medicine Journal 31(8) 649-653.

Bartova (2017) "Robust antidepressant effect following alternating intravenous racemic ketamine and electroconvulsive therapy in treatment-resistant depression: a case report" Journal of ECT 00(00).

Berman et al. (2000) "Antidepressant effects of ketamine in depressed patients" Biol Psychiatry 47:351-354.

Beaudoin et al. (2014) "Low-dose ketamine improves pain relief in patients receiving intravenous opioids for acute pain in the emergency department: results of a randomized, double-blind, clinical trial" Acad Emerg Med 21(11): 1193-1202.

Boulieu (1998) "HPLC determination of ketamine, norketamine, and dehydronorketamine in plasma with a high-purity reversed-phase sorbent" Clinical Chemistry 44(3): 560-564.

Bredlau et al. (2013) "Oral ketamine for children with chronic pain: a pilot phase 1 study" J Pediatr 163(1): 194-200 e191.

Bremner et al. (1998) "Measurement of dissociative states with the clinical-administered dissociative states scale (CADSS)" Journal of Traumatic Stress 11(1).

Brooks (2016) "Repeated ketamine may sustain antidepressant effect" American Journal of Psychiatry.

Brown et al. (1996) "Treatment outcomes for primary care patients with major depression and lifetime anxiety disorders" American Journal of Psychiatry 153(10):1293-1300.

Brunette et al. (2011) "Exploring the pharmacokinetics of oral ketamine in children undergoing burns procedures" Pediatric Anesthetics 21(6):653-662.

Busner (2007) "The clinical global impressions scale: applying a research tool in clinical practice" Psychiatry 4:28-37.

Caddy et al. (2014) "Ketamine as the prototype glutamatergic antidepressant: pharmacodynamic actions and a systematic review and meta-analysis of efficacy" Therapeutic Advances in Psychopharmacology 4(2):75-99.

Cani et al. (2015) "Endocannabinoids—at the crossroads between the gut microbiota and host metabolism" Nature Reviews Endocrinology 12(3): 133-143.

Carliss et al. (2007) "Oral administration of dextromethorphan does not produce neuronal vacuolation in the rat brain" Science Direct Neuro Toxicology 28: 813-818.

Carreno et al. (2016) "Activation of a ventral hippocampus-medial prefrontal cortex pathway is both necessary and sufficient for an antidepressant response to ketamine" Mol Psychiatry 21(9):1298-1308.

Chang et al. (2004) "Mechanisms involved in the antiplatelet activity of ketamine in human platelets" Journal of Biomed Science 11:764-772.

Chen et al. (1998) "Neuroprotective concentrations of the N-methyl D-aspartate open channel blocker memantine are effective without cytoplasmic vacuolation following post-ischemic administration and do not block maze learning or long term potentiation" Neuroscience 86(4):1121-1132.

Chen et al. (2012) "Mechanisms of ketamine-involved regulation of cytochrome P450 gene expression" Expert Opinion Drug Metabolism Toxicology 6(3):273-281.

Chong et al. (2009) "Development of sublingual/oral formulation of ketamine for use in neuropathic pain" Clinical Drug Investigation 29(5):317-324.

Clements, Grant (1981) "Bioavailability, pharmacokinetics, and analgesic activity of ketamine in humans" Journal of Pharmaceutical Sciences 71(5):539-542.

Conway et al. (2017) "Toward an evidence-based, operational definition of treatment-resistant depression, when enough is enough" JAMA Psychiatry 74(1): 9-10.

Correll et al. (2006) "Two case studies of patients with major depressive disorder given low-dose (subanesthetic) ketamine infusions" Pain Medicine 7(1):92-95.

Cox (2019) "Ketamine: Can it really be an antidepressant?" The Guardian, https://theguardian.com/science2019/mar23/ketamine-can-it-really-be-an-antidepressant (pp. 1-7).

Coyle (2013) "Nitric oxide and symptom reduction in Schizophrenia" Jama Psychiatry 70(7):664-5.

Critical review of ketamine 34th ECDD 2006/4.3, Sep. 2002.

Cvrcek (2008) "Side effects of ketamine in the long-term treatment of neuropathic pain" Pain Medicine 9(2):253-257.

Daly et al. (2018) "Efficacy and safety of intranasal esketamine adjunctive to oral antidepressant therapy in treatment-resistant depression: a randomized clinical trial" JAMA psychiatry 75(2):139-148.

Daly et al. (2019) "Efficacy of Esketamine Nasal Spray Plus Oral Antidepressant Treatment for Relapse Prevention in Patients With Treatment-Resistant Depression: A Randomized Clinical Trial" JAMA Psychiatry 76:893-903.

Declaration of Paul William Glue under 37 C.F.R. 1.132 submitted in U.S. Appl. No. 16/362,848 dated Jul. 6, 2020.

Declaration of Zhen shi under 37 C.F.R. 1.132 submitted in U.S. Appl. No. 16/362,848 dated Jul. 6, 2020.

De Gioannis et al. (2014) "Oral ketamine augmentation for chronic suicididality in treatment-resistant depression" Aust N Z J Psychiatry 48(7): 686.

Domino et al. (1982) "Plasma levels of ketamine and two of its metabolites in surgical patients using a gas chromatographic mass fragmentographic assay" Anesthesia and Analgesia 61:87-92.

(56) References Cited

OTHER PUBLICATIONS

Downey et al. (2016) "Comparing the actions of lanicemine and ketamine in depression: key role of the anterior cingulate" European Neuropsychopharmacology 26(6):994-1003.
Duman et al. (2012) "Signaling pathways underlying the rapid antidepressant actions of ketamine" Neuropharmacology 62(1):35-41.
Ebert et al. (1997) "Norketamine: the main metabolite of ketamine is a non-competitive NMDA receptor antagonist in the rat cortex and spinal cord" European Journal of Pharmacology 20(333)(1):99-104.
Emarson (1999) "Clinical experience with oral ketamine" Journal of Pain and Symptom Management 17(5).
Erdil et al. (2015) "Effects of sevoflurane or ketamine on the QTc interval during electroconvulsive therapy" J Anesth 29(2): 180-185.
Fanta et al. (2015) "Population pharmacokinetics of S-ketamine and norketamine in healthy volunteers after intravenous and oral dosing" Eur J Clin Pharmacol 71(4):441-7.
Feder (2014) "Efficacy of intravenous ketamine for treatment of chronic posttraumatic stress disorder" JAMA Psychiatry 71(6):681-688.
Fekadu et al. (2009) "A multidimensional tool to quantify treatment resistance in depression: the Maudsley staging method" Journal of Clinical Psychiatry 70(2):177-184.
Fields et al. (2015) "Pill Properties that Cause Dysphagia and Treatment Failure" Current therapeutic research 77: 79-82.
Fox et al. (2012) "Developmental origins of adult diseases and neurotoxicity: epidemiological and experimental studies" Neurotoxicology 33(4):810-816.
Fredriksson et al. (2004) "Neurobehavioural deficits associated with apoptotic neurodegeneration and vulnerability for ADHD" Neurotoxicity Research 6(6):435-456.
Furuhashi-Yonaha (2002) "Short and long-term efficacy of oral ketamine in eight chronic pain patients" Canadian Journal of Anesthesia 886-887.
Ghasemi et al. (2014) "Rapid antidepressant effects of repeated doses of ketamine compared with electroconvulsive therapy in hospitalized patients with major depressive disorder" Psychiatry Res 215(2): 355-361.
Gills (1995) "Normative values for the beck anxiety inventory, fear questionnaire, Penn State worry questionnaire, and social phobia and anxiety inventory" Psychological Assessment 7(4):450-455.
Glue et al. (2010) "Meta-analysis of relapse prevention antidepressant trials in depressive disorders" Aust NZ J Psychiatry 44:697-705.
Glue et al. (2017) "Ketamine's dose-related effects on anxiety symptoms in patients with treatment refractory anxiety disorders" Journal of Psychopharmacology 31(10):1302-1305.
Glue et al. (2018) "Safety and efficacy of maintenance ketamine treatments in patients with treatment-refractory generalised anxiety and social anxiety disorders" Journal of Psychopharmacology 32(6) https://doi.org/10.1177/0269881118762073.
Glue et al. (2020) "Ascending-dose study of controlled-release ketamine tablets in healthy volunteers, pharmacokinetics, pharmacodynamics, safety, and tolerability" The Journal of Clinical Pharmacology, 60(6): 751-757.
Gough et al. (1995) "Assessment of dose proportionality: report from the statisticians in the pharmaceutical industry/pharmacokinetics UK joint working party" Drug Information Journal 29:1039-1048.
Grande et al. (2016) "(417) Oral ketamine for chronic pain: a 32-subject placebo-controlled trial in patients on chronic opioids" The Journal of Pain 17(4): S78-S79.
Grant (1981) "Pharmacokinetics and analgesic effects of I.M. and oral ketamine" British Journal of Anesthesia 53(8):805-810.
Haile et al. (2014) "Plasma brain derived neurotrophic factor (BDNF) and response to ketamine in treatment-resistant depression" International Journal of Neuropsychopharmacology 17(2):331-336.
Hallak et al. (2013) "Rapid improvement of acute schizophrenia symptoms after intravenous sodium nitroprusside: a randomized, double-blind, placebo-controlled trial" JAMA Psychiatry 70(7):668-676.
Hamilton (1957) "The assessment of anxiety states by rating" Department of Psychiatry, University of Leeds p. 50-55.
Harraz et al. (2016) "Antidepressant action of ketamine via mTOR is mediated by inhibition of nitrergic Rheb degradation" Molecular Psychiatry 21(3):313-9.
Hartberg et al. (2018) "Impact of oral ketamine augmentation on hospital admissions in treatment-resistant depression and PTSD: a retrospective study" Psychopharmacology (Berl) 235(2):393-398.
Hasan et al. (2021) "Chiral Pharmacokinetics and Metabolite Profile of Prolonged-release Ketamine Tablets in Healthy Human Subjects" Anesthesiology 135:326-339.
Hocking, Cousins (2003) "Ketamine in chronic pain management: an evidence-based review" Anesthesia and Analgesia 97(6): 1730-1739.
Horacek (2012) "The influence of clonidine on oral ketaminemidazolam premedication in intellectually disabled patients indicated for . . . " Neuro Endocrinology Letters 33(4):380-384.
Hu et al. (2016) "Single IV ketamine augmentation of newly initiated escitalopram for major depression: results from a randomized, placebo-controlled 4-week study" Psychol Med 46(3): 623-635.
Huang et al. (2016) "Ketamine affects the neurogenesis of the hippocampal dentate gyrus in 7 day old rats" Neurotox Rex 30:185-198.
Humphrey et al. (2012) "The bladder pain/interstitial cystitis symptom score: development, validation, and identification of a cut score" European Association of Urology 61:271-279.
International Search Report dated Sep. 8, 2020 for PCT/IB2020/051909.
International Search Report dated Dec. 27, 2021 for PCT/IB2021/058647.
International Search Report dated Jan. 28, 2019 for PCT/IB2018/057851.
Ionescu et al. (2014) "Effect of baseline anxious depression on initial and sustained antidepressant response to ketamine" J Clin Psychiatry 75(9): e932-938.
Irwin et al. (2010) "Oral ketamine for the rapid treatment of depression and anxiety in patients receiving hospice care" Journal of Palliative Medicine 13(7):903-908.
Irwin (2013) "Daily oral ketamine for the treatment of depression and anxiety in patients receiving hospice care: a 28-day open-label proof-of-concept trial" Journal of Palliative Medicine 16(8):958-965.
Jafarina et al. (2016) "efficacy and safety or oral ketamine versus diclofanec to alleviate mild to moderate depression in chronic pain patients: a double blind, randomized, controlled trial" J affect discord 204:1-8.
Janssen (2000), "Ketamine dreams and realities" Florida, USA, Multidisciplinary Association for Psychedelic Studies (MAPS).
Janssen (2015) "A study of evaluate the efficacy, safety, and tolerability of intranasal eskatimine plus an oral antidepressant in elderly participants with treatment-resistant depression" Transform 3.
Janssen (2015) "Ketamine plus lithium in treatment-resistant depression" Study.
Janssen (2015) "Ketamine trial for the treatment of depression".
Janssen Research and Development (2014) "A double-blind, doubly-randomized, placebo-controlled study of intranasal esketamine in an adaptive treatment protocol to assess safety and efficacy in treatment-resistant depression (Synapse)".
Janssen Research and Development (2015) "A study of ketamine in patients with treatment-resistant depression".
Janssen Research and Development (2015) "A study to evaluate the efficacy, safety, and tolerability of flexible doses of intranasal esketamine plus an oral antidepressant in adult participants with treatment-resistant depression" Transform-2.

(56) References Cited

OTHER PUBLICATIONS

Jarventausta et al. (2013) "Effects of s-ketamine as an anesthetic adjuvant to propofol on treatment response to electroconvulsive therapy in treatment-resistant depression: a randomized pilot study" J ECT 29(3): 158-161.

Jennings et al. (2013) "Oral ketamine for sickle cell crisis pain refractory to opioids" J Pain Palliat Care Pharmacotherapy 27(2): 150-154.

Jevtovice-Todorovic (2001) "A comparative evaluation of neurotoxic properties of ketamine and nitrous oxide" Brain Research 895:264-267.

Kannan, Bhatnagar (2002) "Oral ketamine as an adjuvant to oral morphine for neuropathic pain in cancer patients" Journal of Pain and Symptom Management 23(1):60-65.

Katalinic et al. (2013) "Ketamine as a new treatment for depression: a review of its efficacy and adverse effects" Australian & New Zealand Journal of Psychiatry 47(8): 710-727.

Kessler et al. (2011) The global burden of mental disorders: an update from the WHO world mental health (WMH) surveys Epidemiology and Psychiatric Sciences 18(1):23-33.

Koksal (2015) "Analysis of genotoxic activity of ketamine and rocuronium bromide using the somatic mutation and recombination test in *Drosophila melanogaster*" Environ Toxicol Pharmacol 39(2): 628-634.

Kundra et al. (2013) "Oral ketamine and dexmedetomidine in adults' burns wound dressing—a randomized double blind cross over study" Burns 39(6):1150-1156.

Lai et al. (2014) "Pilot dose-response trial of IV ketamine in treatment-resistant depression" World J Biol Psychiatry 15(7): 579-584.

Lara et al. (2013) "Antidepressant, mood stabilizing and precognitive effects of very low dose sublingual ketamine in refractory unipolar and bipolar depression" International Journal of Neuropsychopharmacology 16(9): 2111-2117.

Leffa et al. (2016) Anesthetic ketamine-induced DNA damage in different cell types in vivo Mol Neurobiol 53(8): 5575-581.

Lenze et al. (2016): "Ninety-six hour ketamine infusion with co-administered clonidine for treatment-resistant depression: a pilot randomised controlled trial" World J Biol Psychiatry 17(3):230-238.

Li et al. (2010) "mTOR-dependent synapse formation underlies the rapid antidepressant effects of NMDA antagonists" Science 329(5994):959-964.

Li et al. (2016) "The effects of low-dose ketamine on the prefrontal cortex and amygdala in treatment-resistant depression: a randomized controlled study" Hum Brain Mapp 37(3): 1080-1090.

Locklear (2016) "Drug quickly quells suicidal thoughts" New Scientist p. 12.

Loo et al. (2012) "Neuropsychological and mood effects of ketamine in electroconvulsive therapy: a randomised controlled trial" J Affect Disord 142(1-3):233-240.

Loo et al. (2016) "Placebo-controlled pilot trial testing dose titration and intravenous, intramuscular, and subcutaneous routes for ketamine in depression" Acta Psychiatry Scand 134(1):48-56, doi 10, 111/acps. 12572, Epub.

Lu et al. (2012) "Sedating pediatric dental patients by oral ketamine with alternating bi-lateral stimulation of eye movement desensitization and minimizing adverse reaction of ketamine by acupuncture and bi-digital o-ring test" Acupuncture & Electro-Therapeutics Research 37(2): 103-123.

Maggi et al. (2002) "Dissolution behaviour of hydrophilic matrix tablets containing two different polyethylene oxides (POs) for the controlled release of a water-soluble drug. Dimensionality study" Biomaterials 23:1113-1119.

Malhi et al. (2009) "Clinical practice recommendations for depression" Acta Psychiatry Scand Supply 439:8-26.

Manji, Mullard (2015) "Husseini Manji" Nat Rev Drug Discovery 14(11): 742-743.

Marchetti et al. (2015) "Efficacy and safety of oral ketamine for the relief of intractable chronic pain: a retrospective 5-year study of 51 patients" Eur J Pain 19(7): 984-993.

Matthew et al. (2012) "Ketamine for treatment-resistant unipolar depression: current evidence" CNS Drugs 26(3): 189-204.

McClintock et al. (2014) "Multifactorial determinants of the neurocognitive effects of electroconvulsive therapy" J ECT 30(2): 165-176.

McNulty (2012) "Compounded oral ketamine for severe depression, anxiety, pain in a hospice patient with end-stage chronic obstructive pulmonary disease, cardiopulmonary failure, and severe renal insufficiency: a case report" International Journal of Pharmaceutical Compounding 16(5):364-386.

Melander et al. (2008) "A regulatory Apologia—a review of placebo-controlled studies in regulatory submissions of new-generation antidepressants" Eur Neuropsychopharmacol 18:623-627.

Meneguz et al. (1999) "Influence of urethane and ketamine on rat hepatic cytochrome P450 in vivo" Exp Toxic Pathol 51:393-396.

Moaddel et al. (2015) "D-serine plasma concentration is a potential biomarker of (R,S)-ketamine antidepressant response in subjects with treatment-resistant depression" Psychopharmacology (Berl) 232(2): 399-409.

Montgomery (1979) "A new depression scale designed to be sensitive to change" British Journal of Psychiatry 134:382-389.

Moreira et al. (2013) "Combined oral midazolam-ketamine better than midazolam alone for sedation of young children: a randomized controlled trial" International Journal of Pediatric Dentistry 23(3):207-215.

Motamed et al. (2012) "Midazolam-ketamine combination for moderate sedation in upper GI endoscopy" Journal of Pediatric Gastroenterology and Nutrition 54(3):422-426.

Mucalo, Rathbone (2012) "Melt-extruded polyethylene oxide (PEO) rods as drug delivery vehicles: formulation, performance as controlled release devices and the influence of co-extruded excipients on drug release profiles" Chemistry in New Zealand: 85-95.

Mundt (2002) "The work and social adjustment scale: impairment in ME and depression study a simple measure of impairment in functioning" British Journal of Psychiatry 180:461-464.

Murrough et al. (2013) "Rapid and longer-term antidepressant effects of repeated Ketamine infusions in treatment-resistant major depression" Biol Psychiatry 74(4):250-256.

Murrough et al. (2015) "Ketamine for rapid reduction of suicidal ideation: a randomized controlled trial" Psychol Med 45(16): 3571-3580.

Nemeroff (2007) "Prevalence and management of treatment-resistant depression" J Clin Psychiatry 68(8):17-25.

Newport et al. (2016) "Whither ketamine as an antidepressant: panacea or toxin" Depression and Anxiety 33(8): 685-688.

Niesters et al. (2014) "Ketamine for chronic pain: risk and benefits" Br J Clin Pharmacology 77(2): 357-367.

Noppers et al. (2011) "Effect of rifampicin on s-ketamine and s-norketamine plasma concentrations in healthy volunteers after intravenous s-ketamine administration" Anesthesiology 114(6): 1435-1445.

Norambuena et al. (2013) "Oral ketamine and midazolam for pediatric burn patients: a prospective, randomized, double-blind study" Journal of Pediatric Surgery 48(3):629-634.

Norouzi et al. (2015) "Comparison of the effects of oral vs. peritonsillar infiltration of ketamine in pain reduction after tonsillectomy: a randomized clinical trial" M.E.J. Anesth 23(1):29-38.

Novicki et al. (1985) "Inhibition of DNA synthesis by chemical carcinogens in cultures of initiated and normal proliferating rat hepatocytes" Cancer Research 45:337-344.

Nunez et al. (2020) "An update on the efficacy and tolerability of oral ketamine for major depression: A systematic review and meta-analysis", Psychopharmacology Bulletin 50(4):137-163.

O'Hara et al. (2014), "A 2 year experience of nurse led conscious sedation in pediatric burns" Burns 40(1): 48-53.

Olney, Price (1989) "Pathological changes induced in cerebrocortical neurons by phencyclidine and related drugs" Science 244: 1360-1362.

Olney et al. (1991) "NMDA antagonist neurotoxicity: mechanism and prevention" Science 254: 1515-1518.

Overall et al. (1984) "The Brief Psychiatric Rating Scale (BPRS) in geropsychiatric research: I. Factor structure on an inpatient unit" J Gerontol 39:187-193.

(56) References Cited

OTHER PUBLICATIONS

Papadimitropoulou et al. (2017) "Comparative efficacy and tolerability of pharmacological and somatic interventions in adult patients with treatment-resistant depression: a systematic review and network meta-analysis" Curr Med Res Opin 33(4): 701-711.
Paslakis et al. (2010) "Oral administration of the NMDA receptor antagonist s-ketamine as add-on therapy of depression: case studies" Pharmacopsychiatry 43(1):33-5.
Paul et al. (2014) "(R-S)-ketamine metabolites (R-S)-norketamine and (2S,6S)-hydroxynorketamine increase the mammalian target of rapamycin function" Anesthesiology 121: 149-159.
Peltoiemi et al. (2012) "S-ketamine concentrations are greatly increased by grapefruit juice" European Journal of Clinical Pharmacology 68(6):979-986.
Peltoiemi et al. (2012) "Rifampicin has a profound effect on the pharmacokinetics of oral s-ketamine and less on intravenous s-ketamine" Basic and Clinical Pharmacology & Toxicology 111: 325-332.
Permoda-Osip et al. (2015) "Single ketamine infusion and neurocognitive performance in bipolar depression" Pharmacopsychiatry 48(2): 78-79.
Posner (2008) "The Columbia-Suicide Severity Rating Scale: initial validity and internal consistency findings from three multisite studies with adolescents and adults" Am J Psychiatry 168(12):1266-77.
Preskorn (2015) "Randomized proof of concept trial of GLYX-13, an N-methyl-D-aspartate receptor glycine site partial agonist, in major depressive disorder nonresponsive to a previous antidepressant agent" J Psychiatry Pract 21(2): 140-149.
Purdue (2009) FDA Advisory Committee on Reformulated Oxycontin FDA.
Rasmussen et al. (2013) "Serial infusions of low-dose ketamine for major depression" Journal of Psychopharmacology 27(5):444-450.
Rasmussen et al. (2014) "A randomized comparison of ketamine versus methohexital anesthesia in electroconvulsive therapy" Psychiatry Res 215(2): 362-365.
Rao et al. (2016) "Role of cytochrome P4502B6 polymorphisms in ketamine metabolism and clearance" Anesthesiology 125(6): 1103-1112.
Rodriguez et al. (2013) "Randomized controlled crossover trial of ketamine in obsessive-compulsive disorder: proof-of-concept" Neuropsychopharmacology 38(12):2475-2483.
Rofael et al. (2003) "Immunomodulation by cocaine and Ketamine in postnatal rats" Toxicology 188:101-114.
Rolan (2016) "Report on preliminary results from study KET-009".
Rush et al. (2006) "Acute and long-term outcomes in depressed outpatients requiring one or several treatment steps: a star'd report" American Journal of Psychiatry 163:1905-1917.
Salvadore et al. (2013) "Ketamine as a fast acting antidepressant: current knowledge and open questions" CNS Neurosci Ther 19(6):428-436.
Sanacora et al. (2014) "Lanicemine: a low-trapping NMDA channel blocker produces sustained antidepressant efficacy with minimal psychotomimetic adverse effects" Mol Psychiatry 19(9): 978-985.
Sanacora et al. (2015) "Ketamine: promising path or false prophecy in the development of novel therapeutics for mood disorders?" Neuropsychopharmacology 40(2):259-267.
Schoevers et al. (2016) "Oral ketamine for the treatment of pain and treatment-resistant depression" The British Journal of Psychiatry 208(2):108-113.
Shillinburg et al. (2017) "Treatment of severe mucositis pain with oral ketamine mouthwash" Support Care Cancer 25(7): 2215-2219.
Shirawi et al. (2017) "Oral ketamine in treatment-resistant depression: a clinical effectiveness case series" J Clin Psychopharmacol 37(4): 464-467.
Sigtermans et al. (2009) "Ketamine produces effective and long-term pain relief in patients with complex regional pain syndrome type 1" Pain 145(3):304-311.
Short et al. (2018) "Side-effects associated with ketamine use in depression: a systematic review" Lancet Psychiatry 5:65-78.
Slikker et al. (2007) "Ketamine-induced neuronal cell death in the perinatal phesus monkey" Toxicology Sciences 98(1): 145-158.
Smeyne et al. (2016) "Assessment of the effects of MPTP and paraquat on dopaminergic neurons and microglia in the substantia nigra pars compacta of C57BL/6 mice" PLoS One 11(10): e0164094.
Smith (2000) "Confidence interval criteria for assessment of dose proportionality" Pharmaceutical Research 17(10):1278-1283.
Sos et al. (2013), "Relationship of ketamine's antidepressant and psychomimetic effects in unipolar depression" Activitas Nervosa Superior Rediviva 34(4): 287-298.
Starte et al. (2012) "Ketamine-associated corneal edema" Cornea 31(5)572-274.
Suehs et al. (2008) "Texas Medication Algorithm Project Procedure" Manual Major Depressive Disorder Algorithms 1-68.
Swiatek et al. (2016) "New use for an old drug: oral ketamine for treatment-resistant depression" BMJ Case Rep 2016.
Teche et al. (2013) "Measurement methods of BDNF levels in major depression: a qualitative systematic review of clinical trials" Psychiatry Q 84(4): 485-497.
The Dow Chemical Company (2014) Reasonable Upper Limit of the Amount of Sentry Polyox.
Viberg et al. (2008) "Neonatal ketamine exposure results in changes in biochemical substrates of neuronal growth and synaptogenisis, and alters adult behavior irreversibly" Toxicology 249: 153-159.
Wang et al. (2012) "Effects of propofol and ketamine as combined anesthesia for electroconvulsive therapy in patients with depressive disorder" J ECT 28(2):128-132.
Wang et al. (2013) "Preclinical assessment of ketamine" CNS Neuroscience Therapy 19(6):448-453.
Wang et al. (2013) Brain damages in ketamine addicts as revealed by magnetic resonance imaging Front Neuroanat 7:23.
Weigand (2000) "Ketamine modulates the stimulated adhesion molecule expression on human neutrophils in vitro" Anesthesia & Analgesia 90:206-212.
Wilson (2011) "Controlled release in oral drug delivery" Advances in Delivery Science and Technology 427 pages.
Wolfson (2016) "The ketamine papers" Science, Therapy, and Transformation 448 pages.
Xu et al. (2016) "Effects of low-dose and very low-dose ketamine among patients with major depression: a systematic review and meta-analysis" International Journal of Neuropsychopharmacology 19(4):1-15.
Yan (2014) "Dual effects of ketamine: neurotoxicity versus neuroprotection in anesthesia for the developing brain" Journal of Neurosurgical Anesthesiology 26(2):155-160.
Yanagihara et al. (2003) "Plasma concentration profiles of ketamine and norketamine after administration of various ketamine preparations to healthy Japanese volunteers" Biopharmaceutics & drug disposition 24(1):37-43.
Yang et al. (2015) "R-ketamine: a rapid-onset and sustained antidepressant without psychotomimetic side effects" Translational Psychiatry 5:e632.
Yoosefi et al. (2014) "Comparing effects of ketamine and thiopental administration during electroconvulsive therapy in patients with major depressive disorder: a randomized, double-blind study" J ECT 30(1): 15-21.
Yuasa et al. (1992) "Influence of anesthetic regimes on intestinal absorption in rats" Pharmaceutical Research 10(6):884-888.
Zanicotti et al. (2013) "Case report: long-term mood response to repeat dose intramuscular ketamine in a depressed patient with advanced cancer" Journal of Palliative Medicine 16(7):1-2.
Zanos et al. (2016) "NMDAR inhibition-independent antidepressant actions of ketamine metabolites" Nature 533(7604):481-486.
Zarate (2017) "Ketamine: translating mechanistic discoveries into the next generation of glutamate modulators for mood disorders" Molecular Psychiatry 22(3):324-327.
Zhang et al. (2016) "Reactive oxygen species-mediated loss of phenotype of parvalbumin interneurons contributes to long term cognitive impairments after repeated neonatal ketamine exposures" Neurotox Res 30: 593-605.

(56) References Cited

OTHER PUBLICATIONS

Zhao et al. (2012) "Simultaneous population pharmacokinetic modelling of ketamine and three major metabolites in patients with treatment-resistant bipolar depression" The British Pharmalogical Society 74(2): 304-314.

Zhao et al. (2014) "Ketamine administered to pregnant rats in the second trimester causes long-lasting behavioral disorders in offspring" Neurobiology of Disease 68:145-155.

Zhao et al. (2017) "Self-assembled ZnO nanoparticle capsules for carrying and delivering isotretinoin to cancer cells" ACS Appl Mater Interfaces 9(22): 18474-18481.

Zuroff et al. (2013) "Consortia-mediated bioprocessing of cellulose to ethanol with a symbiotic Clostridium phytofermentans/yeast co-culture" Biotechnology for Biofuels 6:59.

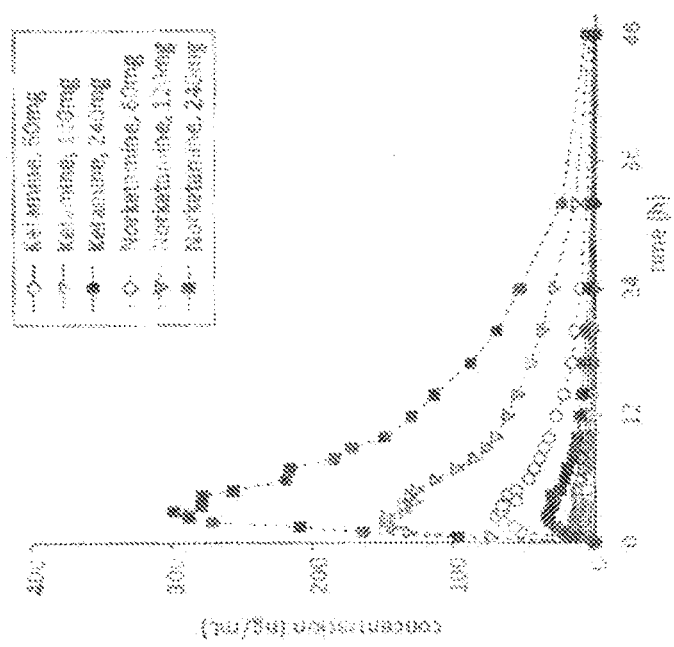

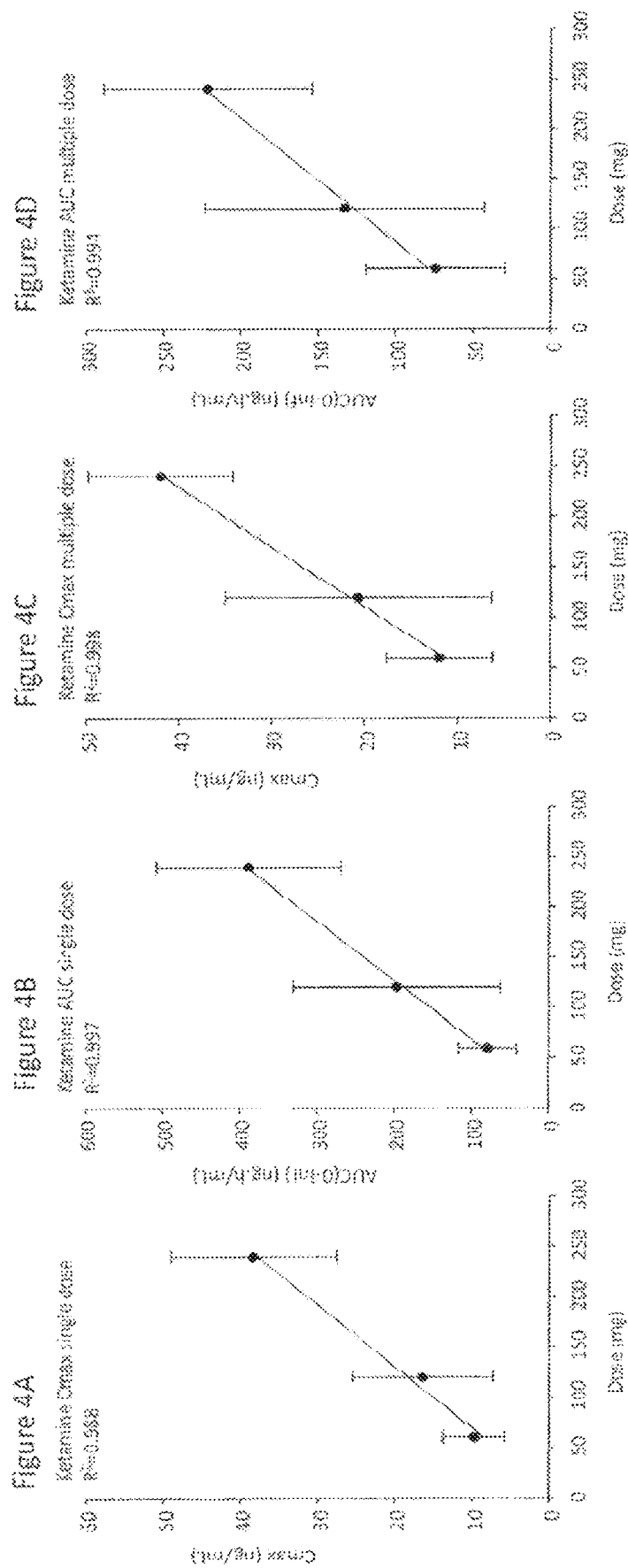

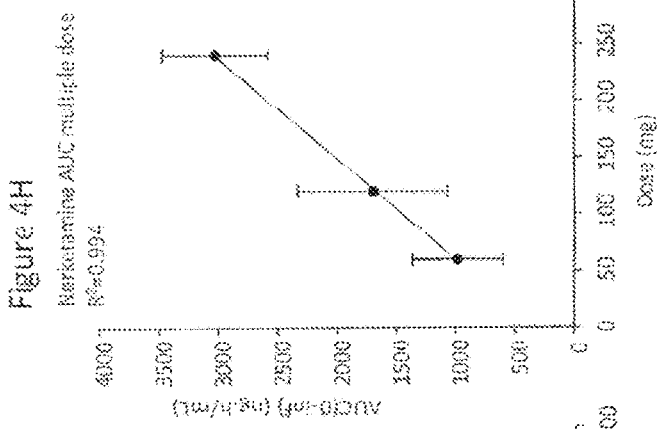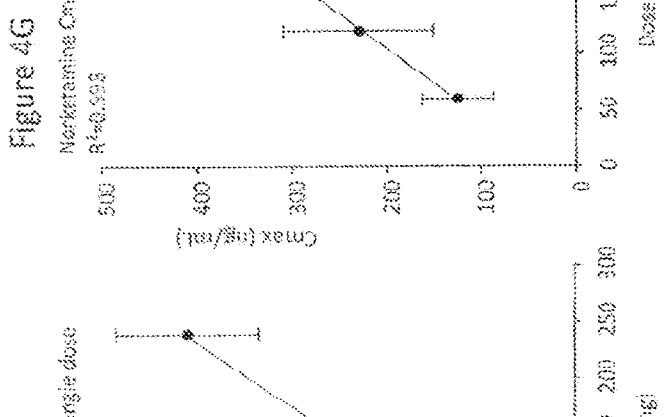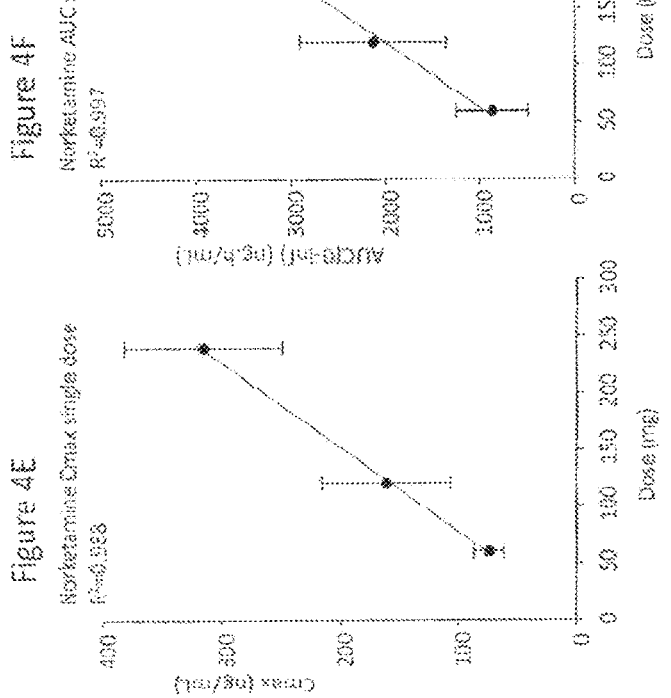

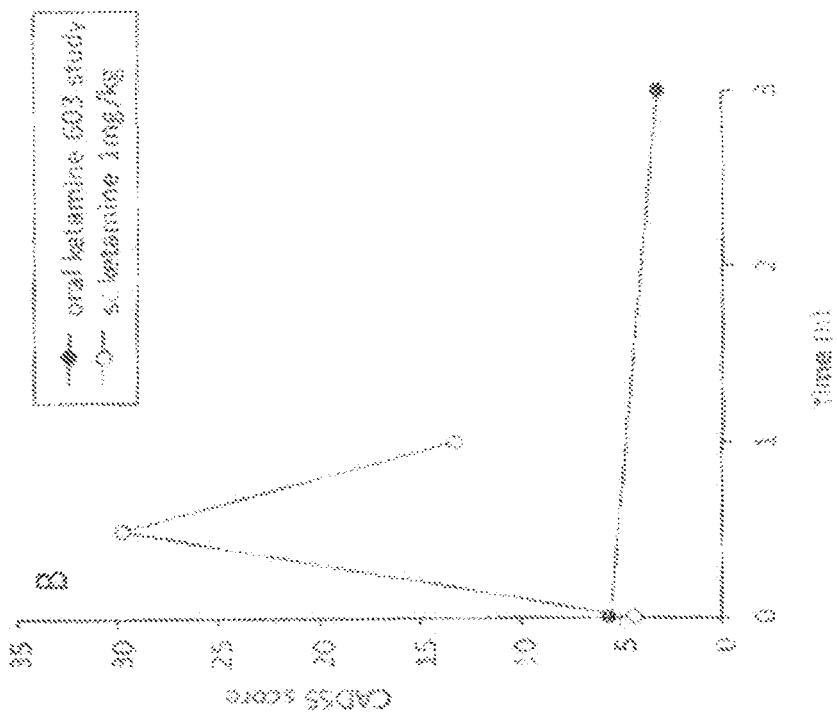
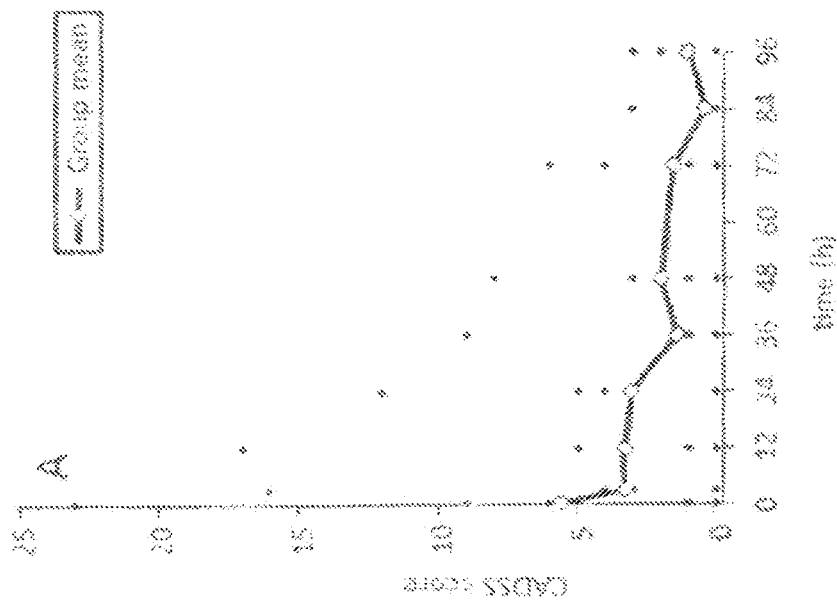

Responders (>50% decline from baseline)

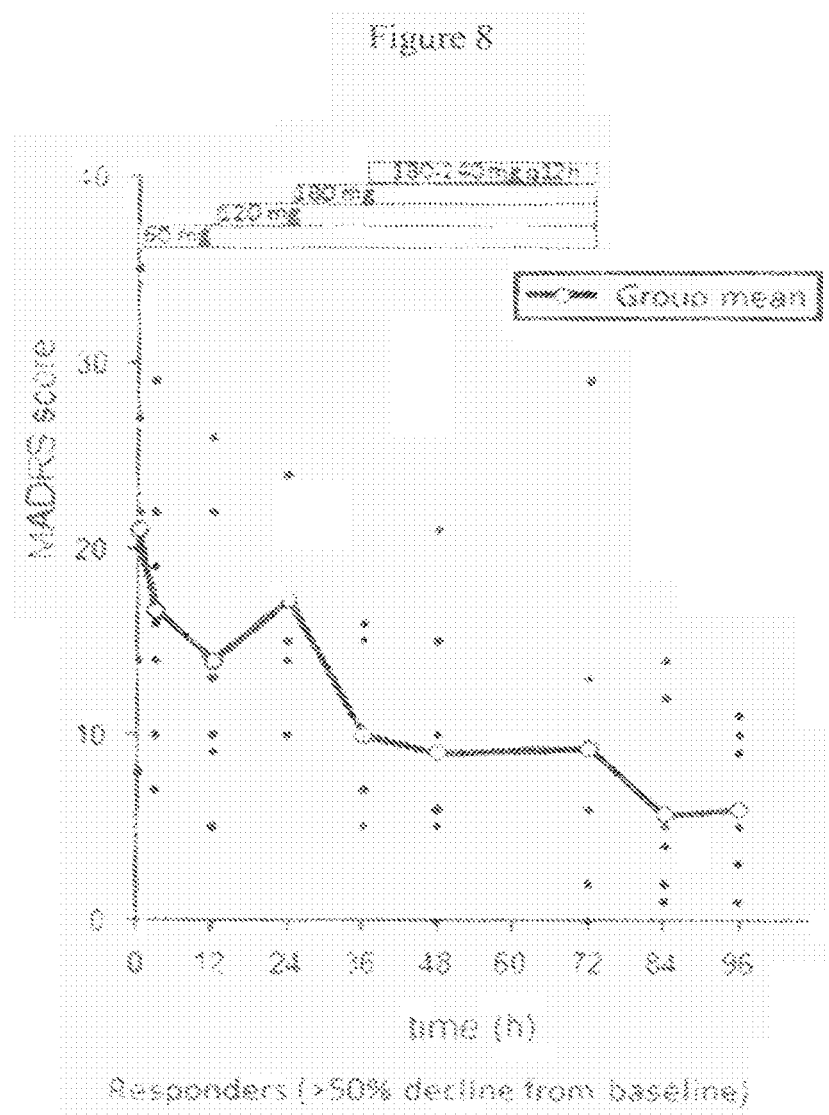

EXTENDED RELEASE PHARMACEUTICAL FORMULATION AND METHODS OF TREATMENT

CROSS-REFERENCE TO RELATED APPLICATIONS

This application is a Continuation of U.S. Ser. No. 16/754,389 filed Apr. 8, 2020, now U.S. Pat. No. 11,471,415 issued Oct. 18, 2022, which is a National Stage application under 35 U.S.C. § 371 of International Application PCT/IB2018/057851 filed on Oct. 10, 2018, which is a continuation-in-part of and claims the benefit under 35 U.S.C. § 120 of application Ser. No. 15/728,695 (now U.S. Pat. No. 10,441,544) filed on Oct. 10, 2017. International Application PCT/IB2018/057851 filed on Oct. 10, 2018, also in turn claims priority under 35 U.S.C. § 119(e) of ASN 62/695,966 filed on Jul. 10, 2018. All of the foregoing applications are incorporated by reference in their entireties.

BACKGROUND OF THE INVENTION

The initial report that low doses of the NMDA antagonist ketamine had rapid onset antidepressant effects in patients with treatment resistant depression (TRD; Berman 2000) has been confirmed in multiple subsequent studies (Xu 2016). More recently ketamine has been shown to have similar rapid-onset activity in a range of treatment-resistant anxiety (TRA) disorders including Post-Traumatic Stress Disorder (PTSD; Feder 2014), Obsessive Compulsive Disorder (OCD; Rodriguez 2013), Generalized Anxiety Disorder (GAD) and Social Anxiety Disorder (SAD; Glue 2017). All of these studies have used injected ketamine, usually given intravenously. There are preliminary case series data suggesting that oral ketamine has antidepressant effects in patients with TRD (Schoevers 2016). The major side effects of injected ketamine include dissociative symptoms that occur mainly in the first hour after dosing, and minor increases in blood pressure and heart rate, which occur in the first 30 minutes. An oral ketamine formulation could minimize these side effects, and be less onerous/time consuming to administer than injected ketamine.

To explore the potential for an oral ketamine formulation to show activity in patients with TRD or TRA, and/or who may suffer from phobias, the inventors developed an extended release ketamine tablet, using a hydrophilic polymeric matrix approach. Polyethylene oxide (PEO) is one of a number of hydrophilic polymers used in controlled drug delivery formulations, and has a number of positive attributes including nontoxicity, high water solubility and swellability (Maggi 2002). Furthermore, tablets formulations based on a high concentration of PEO are able to be annealed (heated) to give tablets of very high hardness that are resistant to crushing. This is a particularly attractive product attribute because ketamine is a drug of abuse. To minimize the potential for dissociative symptoms associated with rapid absorption of ketamine, a prolonged release profile was desirable. The formulation demonstrated linear in vitro dissolution over 10-12 hours. Elimination half-life estimates for ketamine and norketamine for this formulation are much longer that previously reported for tablets.

All references cited herein are incorporated herein by reference in their entireties.

BRIEF SUMMARY OF THE INVENTION

The invention provides a solid, oral, extended release pharmaceutical tablet comprising: (A) a core comprising: i) a therapeutically effective amount of an active agent selected from the group consisting of ketamine, norketamine, pharmaceutically acceptable salts thereof, and combinations thereof; ii) at least one high molecular weight polyethylene oxide (PEO) that is cured, wherein said high molecular weight PEO has an approximate molecular weight of from about 2 million to about 7 million, based upon rheological measurements, and is present in an amount of at least about 30% (by weight) of the core; (B) a coating on said core, wherein said tablet is crush resistant and has a breaking strength of at least about 200 N; and provides a mean $t_{max}$ of said active agent at least about 4 hours after administration of a single tablet to a patient.

The invention provides a tablet wherein the molecular weight of said high molecular weight PEO is selected from the group consisting of at least about 4,000,000; at least about 5,000,000; at least about 6,000,000; and at least about 7,000,000. The invention provides a tablet wherein the active agent comprises at least about 1% (by weight) of the core. The invention provides a tablet wherein said high molecular weight PEO comprises at least about 50% (by weight) of said core. The invention provides a tablet wherein the dosage amount of active agent is selected from the group consisting of about 30 mg, about 60 mg, about 120 mg, and about 240 mg. The invention provides a tablet wherein the tablet is cured at a temperature of about 70° C. to about 75° C. The invention provides a tablet wherein the coating comprises: i) hydroxypropylmethylcellulose; ii) titanium dioxide; and iii) polyethylene glycol. The invention provides a tablet wherein said tablet provides a ketamine $C_{max}$ between about 12 and about 42 ng/mL. The invention provides a tablet wherein said tablet provides a ketamine $AUC_{0-inf}$ between about 79 and about 385 ng·h/mL. The invention provides a tablet wherein said tablet provides a norketamine $C_{max}$ between about 74 and about 315 ng/mL. The invention provides a tablet wherein said tablet provides a norketamine $AUC_{0-inf}$ between about 872 and about 4079 ng·h/mL. The invention provides a tablet wherein the mean $t_{max}$ of said active agent is selected from the group consisting of at least about 4 hours, at least about 6 hours, at least about 8 hours, at least about 10 hours, at least about 11 hours, and at least about 12 hours. The invention provides a tablet wherein the tablet is suitable for once daily administration or twice-daily administration to a patient. The invention provides a tablet wherein the tablet has no or minimal dissociative side effects upon administration to a patient.

The invention provides a method of treating a patient for treatment-resistant depression, comprising: selecting a patient in need of such treatment; and orally administering to the patient a tablet comprising: (A) a core comprising: i) a therapeutically effective amount of an active agent selected from the group consisting of ketamine, norketamine, pharmaceutically acceptable salts thereof, and combinations thereof; ii) at least one high molecular weight polyethylene oxide (PEO) that is cured, wherein said high molecular weight PEO has an approximate molecular weight of from about 2 million to about 7 million, based upon rheological measurements, and is present in an amount of at least about 30% (by weight) of the core; (B) a coating on said core, wherein said tablet is crush resistant and has a breaking strength of at least about 200 N; and provides a mean $t_{max}$ of said active agent at least about 4 hours after administration of a single tablet to a patient, wherein the tablet treats the symptoms of said treatment-resistant depression.

The invention provides a method wherein the molecular weight of said high molecular weight PEO is selected from the group consisting of at least about 2,000,000, at least about 4,000,000; at least about 5,000,000; at least about 6,000,000; and at least about 7,000,000. The invention provides a method wherein the active agent comprises at least about 1% (by weight) of the core. The invention provides a method wherein said high molecular weight PEO comprises at least about 50% (by weight) of said core. The invention provides a method wherein the dosage amount of active agent is selected from the group consisting of about 1 mg, about 2 mg, about 5 mg, about 10 mg, about 30 mg, about 60 mg, about 120 mg, and about 240 mg. 20. The invention provides a method wherein the tablet is cured at a temperature of about 70° C. to about 75° C. The invention provides a method wherein the coating comprises: i) hydroxypropylmethylcellulose; ii) titanium dioxide; and iii) polyethylene glycol. The invention provides a method wherein said tablet provides a ketamine $C_{max}$ between about 12 and about 42 ng/mL. The invention provides a method wherein said tablet provides a ketamine $AUC_{0-inf}$ between about 79 and about 385 ng·h/mL. The invention provides a method wherein said tablet provides a norketamine $C_{max}$ between about 74 and about 315 ng/mL. The invention provides a method wherein said tablet provides a norketamine $AUC_{0-inf}$ between about 872 and about 4079 ng·h/mL. The invention provides a method wherein the mean $t_{max}$ of said active agent is selected from the group consisting of at least about 4 hours, at least about 6 hours, at least about 8 hours, at least about 10 hours, at least about 11 hours, and at least about 12 hours. The invention provides a method wherein the tablet is suitable for once daily administration or twice-daily administration to a patient. The invention provides a method wherein the symptoms of said treatment-resistant depression are alleviated within 2 hours of oral administration of said ketamine. The invention provides a method wherein said method comprises oral administration of a single dose of said ketamine. The invention provides a method wherein said method comprises oral administration of multiple doses of said ketamine. The invention provides a method wherein a single oral administration of said ketamine in doses between 30-180 mg is sufficient to alleviate the effects of said depression for 3-7 days. The invention provides a method wherein tablet has no or minimal dissociative side effects in the patient. The invention provides a method wherein maximal mean improvements in ratings of depressed mood were noted after approximately 6 weeks of maintenance treatment. The invention provides a method further comprising administering a pharmaceutically effective dose of a second or additional agent, wherein said second or additional agent has antidepressant properties.

The invention provides a method wherein said method further comprises an additional therapy selected from: at least one antidepressant selected from the group consisting of citalopram, escitalopram oxalate, fluoxetine, fluvoxamine, paroxetine, sertraline, dapoxetine; venlafaxine and duloxetine; harmaline, iproniazid, isocarboxazid, nialamide, pargyline, phenelzine, selegiline, toloxatone, tranylcypromine, brofaromine, moclobemide; amitriptyline, amoxapine, butriptyline, clomipramine, desipramine, dibenzepin, dothiepin, doxepin, imipramine, iprindole, lofepramine, melitracen, nortriptyline, opipramol, protriptyline, trimipramine; maprotiline, mianserin, nefazodone, trazodone, pharmaceutically acceptable salts, isomers, and combinations thereof; at least one mood stabilizer selected from the group consisting of lithium carbonate, lithium orotate, lithium salt, valproic acid, divalproex sodium, sodium valproate, lamotrigine, carbamazepine, gabapentin, oxcarbazepine, topiramate, pharmaceutically acceptable salts, isomers, and combinations thereof, at least one herbal antidepressants selected from the group consisting of St John's Wort, kava kava, echinacea, saw palmetto, holy basil valerian, milk thistle, Siberian ginseng, Korean ginseng, ashwagandha root, nettle, Ginkgo biloba, gotu kola, ginkgo/gotu kola supreme, astragalus, goldenseal, dong quai, ginseng, St. John's wort supreme, echinacea, bilberry, green tea, hawthorne, ginger, gingko, turmeric, boswellia serata, black cohosh, cats claw, catnip, chamomile, dandelion, chaste tree berry, black elderberry, feverfew, garlic, horse chestnut, licorice, red clover blossom and leaf rhodiola rusa, coleus forskohlii, Passion Flower, eyebright, yohimbe, blueberry plant, black pepper plant, *Hydrocotyle asiatica*, astragalus, valerian poppy root and grape seed, vervain, echinacea ang root, Skull Cap, serenity elixir, and combinations thereof, at least one antipsychotic agent selected from the group consisting of haloperidol, chlorpromazine, fluphenazine, perphenazine, prochlorperazine, thioridazine, trifluoperazine, mesoridazine, promazine, triflupromazine, levomepromazine, promethazine, chlorprothixene, flupenthixol, thiothixene, zuclopenthixol, clozapine, olanzapine, risperidone, quetiapine, ziprasidone, amisulpride, paliperidone, dopamine, bifeprunox, norclozapine, aripiprazole, tetrabenazine, cannabidiol, pharmaceutically acceptable salts, isomers, and combinations thereof; other therapeutic interventions selected from the group consisting of counseling, psychotherapy, cognitive therapy, electroconvulsive therapy, hydrotherapy, hyperbaric oxygen therapy, electrotherapy and electrical stimulation, transcutaneous electrical nerve stimulation ("TENS"), deep brain stimulation, vagus nerve stimulation, and transcranial magnetic stimulation, and combinations thereof.

The invention provides a method of treating a patient for treatment-resistant anxiety, including but not limited to DSM-V Generalized Anxiety Disorder, Social Anxiety Disorder, Panic Disorder, Post-Traumatic Stress Disorder and/or Obsessive-Compulsive Disorder, comprising: selecting a patient in need of such treatment; and orally administering to the patient a tablet comprising: (A) a core comprising: i) a therapeutically effective amount of an active agent selected from the group consisting of ketamine, norketamine, pharmaceutically acceptable salts thereof, and combinations thereof, ii) at least one high molecular weight polyethylene oxide (PEO) that is cured, wherein said high molecular weight PEO has an approximate molecular weight of from about 2 million to about 7 million, based upon rheological measurements, and is present in an amount of at least about 30% (by weight) of the core; (B) a coating on said core, wherein said tablet is crush resistant and has a breaking strength of at least about 200 N; and provides a mean $t_{max}$ of said active agent at least about 4 hours after administration of a single tablet to a patient, wherein the tablet treats the symptoms of said treatment-resistant anxiety. The invention provides a method wherein the molecular weight of said high molecular weight PEO is selected from the group consisting of at least about 2,000,000, at least about 4,000,000; at least about 5,000,000; at least about 6,000,000; and at least about 7,000,000. The invention provides a method wherein the active agent comprises at least about 1% (by weight) of the core. The invention provides a method wherein said high molecular weight PEO comprises at least about 50% (by weight) of said core. The invention provides a method wherein the dosage amount of active agent is selected from the group consisting of about 1 mg, about 2 mg, about 5 mg, about 10 mg, about 30 mg, about 60 mg, about 120 mg, and about 240 mg. The invention provides a method wherein the tablet is cured at a temperature of about 70° C. to about 75° C. The invention provides a method wherein the coating comprises: i) hydroxypropylmethylcellulose; ii) titanium dioxide; and iii) polyethylene glycol. The invention provides a method wherein said tablet provides a ketamine $C_{max}$ between about 12 and about 42 ng/mL. The invention provides a method wherein said tablet provides a ketamine $AUC_{0\text{-}inf}$ between about 79 and about 385 ng·h/mL. The invention provides a method wherein said tablet provides a norketamine $C_{max}$ between about 74 and about 315 ng/mL. The invention provides a method wherein said tablet provides a norketamine $AUC_{0\text{-}inf}$ between about 872 and about 4079 ng·h/mL. The invention provides a method wherein the mean $t_{max}$ of said active agent is selected from the group consisting of at least about 4 hours, at least about 6 hours, at least about 8 hours, at least about 10 hours, at least about 11 hours, and at least about 12 hours. The invention provides a method wherein the tablet is suitable for once daily administration or twice-daily administration to a patient. The invention provides a method wherein the tablet has no or minimal dissociative side effects upon administration to a patient. The invention provides a method wherein the symptoms of said treatment-resistant anxiety are alleviated within 2 hours of oral administration of said ketamine. The invention provides a method wherein said method comprises oral administration of a single dose of said ketamine. The invention provides a method wherein said method comprises oral administration of multiple doses of said ketamine. The invention provides a method wherein a single oral administration of said ketamine in doses between 30-180 mg is sufficient to alleviate the effects of said anxiety for 3-7 days. The invention provides a method wherein maximal mean improvements in ratings of anxious mood were noted after approximately 2 weeks of maintenance treatment. The invention provides a method further comprising administering a pharmaceutically effective dose of a second or additional agent, wherein said second or additional agent is has antianxiety properties. The invention provides a method which further comprises an additional therapy selected from: at least one antidepressant selected from the group consisting of citalopram, escitalopram oxalate, fluoxetine, fluvoxamine, paroxetine, sertraline, dapoxetine, venlafaxine and duloxetine, harmaline, iproniazid, isocarboxazid, nialamide, pargyline, phenelzine, selegiline, toloxatone, tranylcypromine, brofaromine, moclobemide, amitriptyline, amoxapine, butriptyline, clomipramine, desipramine, dibenzepin, dothiepin, doxepin, imipramine, iprindole, lofepramine, melitracen, nortriptyline, opipramol, protriptyline, trimipramine, maprotiline, mianserin, nefazodone, trazodone, pharmaceutically acceptable salts, isomers, and combinations thereof, at least one serotonin 1a partial agonist selected from the group consisting of buspirone, eltoprazine, or tandospirone, pharmaceutically acceptable salts, isomers, and combinations thereof, at least one alpha-2-delta ligand selected from the group consisting of gabapentin, pregabalin, 3-methylgabapentin, (1alpha,3 alpha,5alpha)(3-amino-methyl-bicyclo[3.2.0]hept-3-yl)-acetic acid, (3S,5R)-3 aminomethyl-5 methyl-heptanoic acid, (3S,5R)-3 amino-5 methyl-heptanoic acid, (3S,5R)-3 amino-5 methyl-octanoic acid, (2S,4S)-4-(3-chlorophenoxy)proline, (2S,4S)-4-(3-fluorobenzyl)-proline, [(1R,5R,6 S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methyl-amine, (3S,4S)-(1-aminomethyl-3,4-dimethyl-cyclopentyl)-acetic acid, (3S,5R)-3 aminomethyl-5 methyl-octanoic acid, (3S,5R)-3 amino-5 methyl-nonanoic acid, (3S,5R)-3 amino-5 methyl-octanoic acid, (3R,4R,5R)-3-amino-4,5-dimethyl-heptanoic acid and (3R,4R,5R)-3-amino-4,5-dimethyl-octanoic acid, pharmaceutically acceptable salts, isomers, and combinations thereof; at least one antiadrenergic agents selected from the group consisting of clonidine, prazosin, propranolol, fuanfacine, methyldopa, guanabenz, doxazosin, prazosin, terazosin, silodosin, alfuzosin, tamsulosin, dutasertide/tamsulosin, guanadrel, mecemylamine, guanethidine, pharmaceutically acceptable salts, isomers, and combinations thereof; at least one benzodiazepine agent selected from the group consisting of alprazolam, bromazepam, chlordiazepoxide, clobazam, clonazepam, clorazepate, diazepam, midazolam, lorazepam, nitrazepam, temazepam, nimetazepam, estazolam, flunitrazepam, oxazepam, triazolam, pharmaceutically acceptable salts, isomers, and combinations thereof; at least one antipsychotic agent selected from the group consisting of haloperidol, chlorpromazine, fluphenazine, perphenazine, prochlorperazine, thioridazine, trifluoperazine, mesoridazine, promazine, triflupromazine, levomepromazine, promethazine, chlorprothixene, flupenthixol, thiothixene, zuclopenthixol, clozapine, olanzapine, risperidone, quetiapine, ziprasidone, amisulpride, paliperidone, dopamine, bifeprunox, norclozapine, aripiprazole, tetrabenazine, cannabidiol, pharmaceutically acceptable salts, isomers, and combinations thereof; other therapeutic interventions selected from the group consisting of counseling, psychotherapy, cognitive therapy, electroconvulsive therapy, hydrotherapy, hyperbaric oxygen therapy, electrotherapy and electrical stimulation, transcutaneous electrical nerve stimulation ("TENS"), deep brain stimulation, vagus nerve stimulation, and transcranial magnetic stimulation, and combinations thereof.

The invention provides a method of treating a patient for DSM-5 Specific Phobia, the method comprising the steps of: selecting a patient in need of such treatment; and administering ketamine to the patient in a dosage form selected from the group consisting of a subcutaneous injection, an intramuscular injection, an intravenous infusion, a controlled release tablet, a lozenge, a sublingual formulation, an intranasal spray, combinations thereof, and any other effective route of administration. The invention provides a method wherein the dosage amount of ketamine is selected from the group consisting of about 1 mg, about 2 mg, about 5 mg, about 10 mg, about 30 mg, about 60 mg, about 120 mg, and about 240 mg. The invention provides a method wherein the dosing frequency of the ketamine formulation ranges from once weekly, twice weekly, three times weekly, up to daily administration to a patient. The invention provides a method wherein the DSM-5 Specific Phobia is selected from the group consisting of environmental phobia, animal phobia, situational phobia, bodily phobia, and combinations thereof. The invention provides a method wherein the environmental phobia is selected from the group consisting of fear of germs, deep water, heights, and other environmental phobias, and combinations thereof. The invention provides a method wherein the animal phobia is selected from the group consisting of fear of dogs, spiders, snakes, other animal phobias, and combinations thereof. The invention provides a method wherein the situational phobia is selected from the group consisting of fear of flying in an aeroplane, visiting the dentist, other situational phobias, and combinations thereof. The invention provides a method wherein the bodily phobia is selected from the group consisting of fear of blood exposure, other bodily phobias, and combinations thereof. The invention provides a method wherein the symptoms of said specific phobia are alleviated within 1-3 hours of administration of said ketamine formulations. The invention provides a method wherein said method comprises single dose administration of said ketamine formulations. The invention provides a method wherein said method comprises multiple dose administrations of said ketamine formulations. The invention provides a method wherein a single administration of said ketamine formulations in doses between 30-180 mg is sufficient to alleviate the effects of said phobic anxiety and avoidance for 3-7 days. The invention provides a method wherein maximal mean improvements in ratings of said phobic anxiety and avoidance were noted after approximately 2 weeks of maintenance treatment. The invention provides a method further comprising administering a pharmaceutically effective dose of a second or additional agent, wherein said second or additional agent is has antianxiety properties. The invention provides a method wherein which further comprises an additional therapy selected from: at least one antidepressant selected from the group consisting of citalopram, escitalopram oxalate, fluoxetine, fluvoxamine, paroxetine, sertraline, dapoxetine, venlafaxine and duloxetine, harmaline, iproniazid, isocarboxazid, nialamide, pargyline, phenelzine, selegiline, toloxatone, tranylcypromine, brofaromine, moclobemide, amitriptyline, amoxapine, butriptyline, clomipramine, desipramine, dibenzepin, dothiepin, doxepin, imipramine, iprindole, lofepramine, melitracen, nortriptyline, opipramol, protriptyline, trimipramine, agomelatine, maprotiline, mianserin, nefazodone, trazodone, pharmaceutically acceptable salts, isomers, and combinations thereof, at least one serotonin 1a partial agonist selected from the group consisting of buspirone, eltoprazine, or tandospirone, pharmaceutically acceptable salts, isomers, and combinations thereof, at least one alpha-2-delta ligand selected from the group consisting of gabapentin, pregabalin, 3-methylgabapentin, (1alpha,3 alpha,5alpha)(3-amino-methyl-bicyclo[3.2.0]hept-3-yl)-acetic acid, (3S,5R)-3 aminomethyl-5 methyl-heptanoic acid, (3S,5R)-3 amino-5 methyl-heptanoic acid, (3S,5R)-3 amino-5 methyl-octanoic acid, (2S,4S)-4-(3-chlorophenoxy)proline, (2S,4S)-4-(3-fluorobenzyl)-proline, [(1R,5R, 6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methyl-amine, (3S,4 S)-(1-aminomethyl-3,4-dimethyl-cyclopentyl)-acetic acid, (3S,5R)-3 aminomethyl-5 methyl-octanoic acid, (3S,5R)-3 amino-5 methyl-nonanoic acid, (3S,5R)-3 amino-5 methyl-octanoic acid, (3R,4R,5R)-3-amino-4,5-dimethyl-heptanoic acid and (3R,4R,5R)-3-amino-4,5-dimethyl-octanoic acid, pharmaceutically acceptable salts, isomers, and combinations thereof; at least one antiadrenergic agents selected from the group consisting of clonidine, prazosin, propranolol, fuanfacine, methyldopa, guanabenz; doxazosin, prazosin, terazosin, silodosin, alfuzosin, tamsulosin, dutasteride/tamsulosin, guanadrel, mecemylamine, guanethidine, pharmaceutically acceptable salts, isomers, and combinations thereof; at least one benzodiazepine agent selected from the group consisting of alprazolam, bromazepam, chlordiazepoxide, clobazam, clonazepam, clorazepate, diazepam, midazolam, lorazepam, nitrazepam, temazepam, nimetazepam, estazolam, flunitrazepam, oxazepam (Serax), temazepam, Restoril, Normison, Planum, Tenox, Temaze, triazolam, pharmaceutically acceptable salts, isomers, and combinations thereof; at least one antipsychotic agent selected from the group consisting of haloperidol, chlorpromazine, fluphenazine, perphenazine, prochlorperazine, thioridazine, trifluoperazine, mesoridazine, promazine, triflupromazine, levomepromazine, promethazine, chlorprothixene, flupenthixol, thiothixene, zuclopenthixol, clozapine, olanzapine, risperidone, quetiapine, ziprasidone, amisulpride, paliperidone, dopamine, bifeprunox, norclo-zapine, aripiprazole, tetrabenazine, cannabidiol, pharmaceutically acceptable salts, isomers, and combinations thereof; other therapeutic interventions selected from the group consisting of counseling, psychotherapy, cognitive therapy, exposure and other behavioural therapies electroconvulsive therapy, hydrotherapy, hyperbaric oxygen therapy, electrotherapy and electrical stimulation, transcutaneous electrical nerve stimulation ("TENS"), deep brain stimulation, vagus nerve stimulation, and transcranial magnetic stimulation, and combinations thereof.

The invention provides for the use of the compositions of the invention for the production of a medicament for treating the indications as set forth herein.

In accordance with a further embodiment, the present invention provides a use of the pharmaceutical compositions described herein, in an amount effective for use in a medicament, and most preferably for use as a medicament for treating a disease or disorder in a subject.

In accordance with yet another embodiment, the present invention provides a use of the pharmaceutical compositions described herein, and at least one additional therapeutic agent, in an amount effective for use in a medicament, and most preferably for use as a medicament for treating a disease or disorder associated with disease in a subject.

The invention provides a method of treating a patient for DSM-5 Specific Phobia, comprising: selecting a patient in need of such treatment; and orally administering to the patient a tablet comprising: (A) a core comprising: i) a therapeutically effective amount of an active agent selected from the group consisting of ketamine, norketamine, pharmaceutically acceptable salts thereof, and combinations thereof; ii) at least one high molecular weight polyethylene oxide (PEO) that is cured, wherein said high molecular weight PEO has an approximate molecular weight of from about 2 million to about 7 million, based upon rheological measurements, and is present in an amount of at least about 30% (by weight) of the core; (B) a coating on said core, wherein said tablet is crush resistant and has a breaking strength of at least about 200 N; and provides a mean $t_{max}$ of said active agent at least about 4 hours after administration of a single tablet to a patient, wherein the tablet treats the symptoms of said DSM-5 Specific Phobia. The invention provides a method wherein the molecular weight of said high molecular weight PEO is selected from the group consisting of at least about 2,000,000, at least about 4,000,000; at least about 5,000,000; at least about 6,000,000; and at least about 7,000,000. The invention provides a method wherein the active agent comprises at least about 1% (by weight) of the core. The invention provides a method wherein said high molecular weight PEO comprises at least about 50% (by weight) of said core. The invention provides a method wherein the dosage amount of active agent is selected from the group consisting of about 1 mg, about 2 mg, about 5 mg, about 10 mg, about 30 mg, about 60 mg, about 120 mg, and about 240 mg. The invention provides a method wherein the tablet is cured at a temperature of about 70° C. to about 75° C. The invention provides a method wherein the coating comprises: i) hydroxypropylmethylcellulose; ii) titanium dioxide; and iii) polyethylene glycol. The invention provides a method wherein said tablet provides a ketamine $C_{max}$ between about 12 and about 42 ng/mL. The invention provides a method wherein said tablet provides a ketamine $AUC_{0-inf}$ between about 79 and about 385 ng·h/mL. The invention provides a method wherein said tablet provides a norketamine $C_{max}$ between about 74 and about 315 ng/mL. The invention provides a method wherein said tablet provides a norketamine $AUC_{0-inf}$ between about 872 and about 4079 ng·h/mL. The invention provides a method wherein the mean $t_{max}$ of said active agent is selected from the group consisting of at least about 4 hours, at least about 6 hours, at least about 8 hours, at least about 10 hours, at least about 11 hours, and at least about 12 hours. The invention provides a method wherein the tablet is suitable for once daily administration or twice-daily administration to a patient. The invention provides a method wherein the symptoms of said DSM-5 Specific Phobia are alleviated within 2 hours of oral administration of said ketamine. The invention provides a method wherein said method comprises oral administration of a single dose of said ketamine. The invention provides a method wherein said method comprises oral administration of multiple doses of said ketamine.

The invention provides a method wherein a single oral administration of said ketamine in doses between 30-180 mg is sufficient to alleviate the effects of said DSM-5 Specific Phobia for 3-7 days. The invention provides a method wherein tablet has no or minimal dissociative side effects in the patient. The invention provides a method wherein the dosing frequency of the ketamine formulation ranges from once weekly, twice weekly, three times weekly, up to daily administration to a patient. The invention provides a method wherein the DSM-5 Specific Phobia is selected from the group consisting of environmental phobia, animal phobia, situational phobia, bodily phobia, and combinations thereof. The invention provides a method wherein the environmental phobia is selected from the group consisting of fear of germs, deep water, heights, other environmental phobias, and combinations thereof. The invention provides a method wherein the animal phobia is selected from the group consisting of fear of dogs, spiders, snakes, other animal phobias, and combinations thereof. The invention provides a method wherein the situational phobia is selected from the group consisting of fear of flying in an aeroplane, visiting the dentist, other situational phobias, and combinations thereof. The invention provides a method wherein the bodily phobia is selected from the group consisting of fear of blood exposure, other bodily phobias, and combinations thereof. The invention provides a method wherein the symptoms of said specific phobia are alleviated within 1-3 hours of administration of said ketamine formulations. The invention provides a method wherein said method comprises single dose administration of said ketamine formulations. The invention provides a method wherein said method comprises multiple dose administrations of said ketamine formulations. The invention provides a method wherein a single administration of said ketamine formulations in doses between 30-180 mg is sufficient to alleviate the effects of said phobic anxiety and avoidance for 3-7 days. The invention provides a method wherein maximal mean improvements in ratings of DSM-5 Specific Phobia were noted after approximately 2 weeks of maintenance treatment. The invention provides a method further comprising administering a pharmaceutically effective dose of a second or additional agent, wherein said second or additional agent is has antianxiety properties. The invention provides a method wherein said method further comprises an additional therapy selected from: at least one antidepressant selected from the group consisting of citalopram, escitalopram oxalate, fluoxetine, fluvoxamine, paroxetine, sertraline, dapoxetine; venlafaxine and duloxetine; harmaline, iproniazid, isocarboxazid, nialamide, pargyline, phenelzine, selegiline, toloxatone, tranylcypromine, brofaromine, moclobemide; amitriptyline, amoxapine, butriptyline, clomipramine, desipramine, dibenzepin, dothiepin, doxepin, imipramine, iprindole, lofepramine, melitracen, nortriptyline, opipramol, protriptyline, trimipramine; agomelatine, maprotiline, mianserin, nefazodone, trazodone, pharmaceutically acceptable salts, isomers, and combinations thereof; at least one serotonin 1a partial agonist selected from the group consisting of buspirone, eltoprazine, or tandospirone, pharmaceutically acceptable salts, isomers, and combinations thereof; at least one alpha-2-delta ligand selected from the group consisting of gabapentin, pregabalin, 3-methylgabapentin, (1alpha,3 alpha,5alpha)(3-amino-methyl-bicyclo[3.2.0]hept-3-yl)-acetic acid, (3S, 5R)-3 aminomethyl-5 methyl-heptanoic acid, (3S,5R)-3 amino-5 methyl-heptanoic acid, (3S,5R)-3 amino-5 methyl-octanoic acid, (2S,4S)-4-(3-chlorophenoxy)proline, (2S, 4S)-4-(3-fluorobenzyl)-proline, [(1R,5R,6 S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3 aminomethyl-5 methyl-octanoic acid, (3S,5R)-3 amino-5 methyl-nonanoic acid, (3S,5R)-3 amino-5 methyl-octanoic acid, (3R,4R,5R)-3-amino-4,5-dimethyl-heptanoic acid and (3R,4R,5R)-3-amino-4,5-dimethyl-octanoic acid, pharmaceutically acceptable salts, isomers, and combinations thereof; at least one antiadrenergic agents selected from the group consisting of clonidine, prazosin, propranolol, fuanfacine, methyldopa, guanabenz; doxazosin, prazosin, terazosin, silodosin, alfuzosin, tamsulosin, dutasertide/tamsulosin, guanadrel, mecemylamine, guanethidine, pharmaceutically acceptable salts, isomers, and combinations thereof; at least one benzodiazepine agent selected from the group consisting of alprazolam, bromazepam, chlordiazepoxide, clobazam, clonazepam, clorazepate, diazepam, midazolam, lorazepam, nitrazepam, temazepam, nimetazepam, estazolam, flunitrazepam, oxazepam (Serax), temazepam, Restoril, Normison, Planum, Tenox, Temaze, triazolam, pharmaceutically acceptable salts, isomers, and combinations thereof; at least one antipsychotic agent selected from the group consisting of haloperidol, chlorpromazine, fluphenazine, perphenazine, prochlorperazine, thioridazine, trifluoperazine, mesoridazine, promazine, triflupromazine, levomepromazine, promethazine, chlorprothixene, flupenthixol, thiothixene, zuclopenthixol, clozapine, olanzapine, risperidone, quetiapine, ziprasidone, amisulpride, paliperidone, dopamine, bifeprunox, norclozapine, aripiprazole, tetrabenazine, cannabidiol, pharmaceutically acceptable salts, isomers, and combinations thereof; other therapeutic interventions selected from the group consisting of counseling, psychotherapy, cognitive therapy, exposure and other behavioural therapies electroconvulsive therapy, hydrotherapy, hyperbaric oxygen therapy, electrotherapy and electrical stimulation, transcutaneous electrical nerve stimulation ("TENS"), deep brain stimulation, vagus nerve stimulation, and transcranial magnetic stimulation, and combinations thereof.

BRIEF DESCRIPTION OF SEVERAL VIEWS OF THE DRAWINGS

The invention will be described in conjunction with the following drawings in which like reference numerals designate like elements and wherein:

FIG. 3A is a chart showing mean concentration-time profiles of ketamine and norketamine after single dose, Cohorts 1-3; FIG. 3B is a chart showing mean concentration-time profiles of ketamine and norketamine after multiple doses, Cohorts 1-3.

FIG. 4A is a chart showing ketamine maximum concentration ($C_{max}$) dose-proportionality after single doses of 60 mg, 120 mg and 240 mg extended release ketamine tablets; FIG. 4B is a chart showing ketamine Area under the Concentration-Time curve (AUC) after single doses of 60 mg, 120 mg and 240 mg extended release ketamine tablets; FIG. 4C is a chart showing ketamine maximum concentration ($C_{max}$) dose-proportionality after multiple doses of 60 mg, 120 mg and 240 mg extended release ketamine tablets; FIG. 4D is a chart showing ketamine Area under the Concentration-Time curve (AUC) after multiple doses of 60 mg, 120 mg and 240 mg extended release ketamine tablets; FIG. 4E is a chart showing norketamine maximum concentration ($C_{max}$) dose-proportionality after single doses of 60 mg, 120 mg and 240 mg extended release norketamine tablets; FIG. 4F is a chart showing norketamine Area under the Concentration-Time curve (AUC) after single doses of 60 mg, 120 mg and 240 mg extended release norketamine tablets; FIG. 4G is a chart showing norketamine maximum concentration ($C_{max}$) dose-proportionality after multiple doses of 60 mg, 120 mg and 240 mg extended release norketamine tablets; FIG. 4H is a chart showing norketamine Area under the Concentration-Time curve (AUC) after multiple doses of 60 mg, 120 mg and 240 mg extended release norketamine tablets, Cohorts 1-3.

FIG. 5A is a chart showing the individual and mean CADSS scores, Cohort 4 after dosing with extended release ketamine tablets. FIG. 5B is a chart showing the comparison of mean CADS S scores over 3 hours after initial dosing with ketamine tablets (filled symbols) and subcutaneous ketamine (open symbols) in the 6 Cohort 4 participants with both sets of data.

FIG. 8 is a chart showing individual and mean Montgomery-Asberg Depression Rating Scale (MADRS) scores, Cohort 4 after dosing with extended release ketamine tablets.

DETAILED DESCRIPTION OF THE INVENTION

Figure 1:
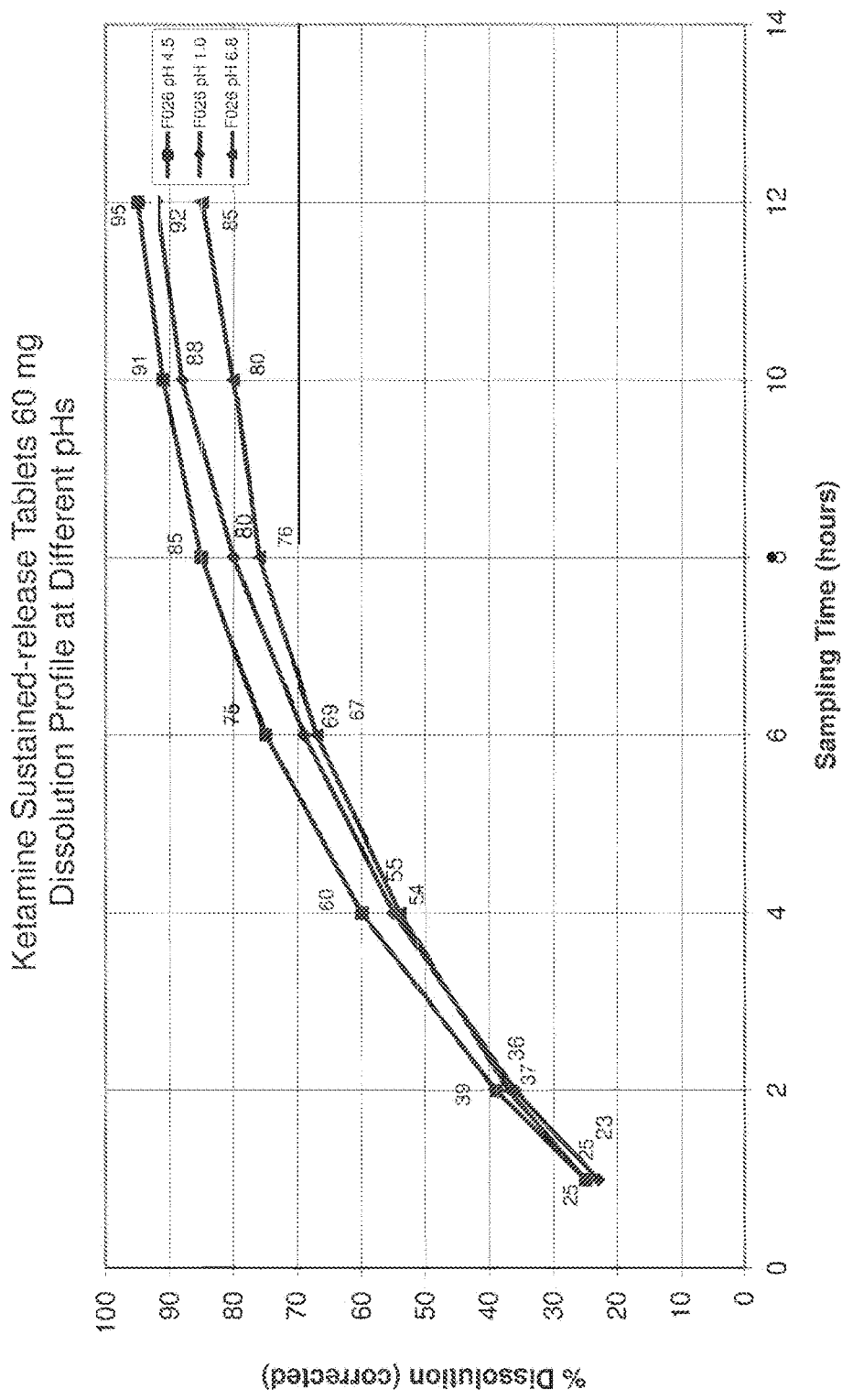
FIG. 1 is a chart showing dissolution profiles of the 60 mg sustained release ketamine tablet at 3 different pHs.

As used herein the term "active pharmaceutical ingredient" ("API") or "pharmaceutically active agent" is a drug or agent which can be employed for the invention and is intended to be used in the human or animal body in order to heal, to alleviate, to prevent or to diagnose diseases, ailments, physical damage or pathological symptoms; allow the state, the condition or the functions of the body or mental states to be identified; to replace active substances produced by the human or animal body, or body fluids; to defend against, to eliminate or to render innocuous pathogens, parasites or exogenous substances or to influence the state, the condition or the functions of the body or mental states. Drugs in use can be found in reference works such as, for example, the Rote Liste or the Merck Index. Examples which may be mentioned include ketamine.

An amount is "effective" as used herein, when the amount provides an effect in the subject. As used herein, the term "effective amount" means an amount of a compound or composition sufficient to significantly induce a positive benefit, including independently or in combinations the benefits disclosed herein, but low enough to avoid serious side effects, i.e., to provide a reasonable benefit to risk ratio, within the scope of sound judgment of the skilled artisan. For those skilled in the art, the effective amount, as well as dosage and frequency of administration, may easily be determined according to their knowledge and standard methodology of merely routine experimentation based on the present disclosure.

As used herein, the terms "subject" and "patient" are used interchangeably. As used herein, the term "patient" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is an elderly human. In another embodiment, the subject is a human adult. In another embodiment, the subject is a human child. In yet another embodiment, the subject is a human infant.

As used herein, the phrase "pharmaceutically acceptable" means approved by a regulatory agency of the federal or a state government, or listed in the U.S. Pharmacopeia, European Pharmacopeia, or other generally recognized pharmacopeia for use in animals, and more particularly, in humans.

As used herein, the term "excipient" means the substances used to formulate active pharmaceutical ingredients (API) into pharmaceutical formulations; in a preferred embodiment, an excipient does not lower or interfere with the primary therapeutic effect of the API. Preferably, an excipient is therapeutically inert. The term "excipient" encompasses carriers, diluents, vehicles, solubilizers, stabilizers, bulking agents, acidic or basic pH-adjusting agents and binders. Excipients can also be those substances present in a pharmaceutical formulation as an indirect or unintended result of the manufacturing process. Preferably, excipients are approved for or considered to be safe for human and animal administration, i.e., GRAS substances (generally regarded as safe). GRAS substances are, for example, listed by the U.S. Food and Drug administration in the Code of Federal Regulations (CFR) at 21 CFR 182 and 21 CFR 184, incorporated herein by reference.

As used herein, the terms "prevent," "preventing" and "prevention" in the context of the administration of a therapy to a subject refer to the prevention or inhibition of the recurrence, onset, and/or development of a disease or condition, or a combination of therapies (e.g., a combination of prophylactic or therapeutic agents).

As used herein, the terms "therapies" and "therapy" can refer to any method(s), composition(s), and/or agent(s) that can be used in the prevention, treatment and/or management of a disease or condition, or one or more symptoms thereof.

As used herein, the terms "treat," "treatment," and "treating" in the context of the administration of a therapy to a subject refer to the reduction or inhibition of the progression and/or duration of a disease or condition, the reduction or amelioration of the severity of a disease or condition, and/or the amelioration of one or more symptoms thereof resulting from the administration of one or more therapies.

As used herein, the term "about" when used in conjunction with a stated numerical value or range has the meaning reasonably ascribed to it by a person skilled in the art, i.e. denoting somewhat more or somewhat less than the stated value or range.

Administration: The application or delivery of a drug to a patient in need of the drug. This term is intended to include any means of administration which accomplishes the application or delivery of the drug (i.e., topical, oral, aerosol, suppository, parenteral, e.g., intravenous, intramuscular, subcutaneous injection, e.g., into the tissue, intraperitoneally and the like). The term is also intended to include any means necessary to accomplish such administration. The term is further intended to include the in vivo production of a drug or aggregation of a drug moderated by another substance such as an enzyme or enzyme gene to affect production of a drug or its precursors.

Depression

Depression is characterized by depressed mood, and markedly diminished interest or pleasure in activities. Other symptoms include significant weight loss or weight gain, decrease or increase in appetite, insomnia or hypersomnia, psychomotor agitation or retardation, fatigue or loss of energy, feelings of worthlessness or excessive or inappropriate guilt, diminished ability to think or concentrate or indecisiveness, recurrent thoughts of death, suicidal ideation or suicidal attempts. A variety of somatic symptoms may also be present. Though depressive feelings are common, especially after experiencing setbacks in life, depressive disorder is diagnosed only when the symptoms reach a threshold and last at least two weeks. Depression can vary in severity from mild to very severe. It is most often episodic but can be recurrent or chronic. Some people have only a single episode, with a full return to premorbid function. However, more than 50 percent of those who initially suffer a single major depressive episode eventually develop another.

Treatment resistant-depression includes unipolar depression that does not respond satisfactorily to one or more treatments that are optimally delivered. If the depression has not benefited from at least two adequate trials of medications from different classes in the current episode, clinically significant treatment resistance is present.

Any chronic, treatment-resistant depression may be treated by the methods described herein. Such depression may include but is not limited to any of: major depressive disorder, single episode, recurrent major depressive disorder-unipolar depression, seasonal affective disorder-winter depression, bipolar mood disorder-bipolar depression, mood disorder due to a general medical condition—with major depressive-like episode, or mood disorder due to a general medical condition—with depressive features, wherein those disorders are resistant to treatment in a given patient. Thus, any patient that presents one of those disorders and who has not responded to an adequate trial of one antidepressant in the current episode and has recurrent or chronic depressive symptoms for greater than 2 years can be treated by the methods of the invention. Manic Depressive illnesses are also described in Goodwin, et al. 2007.

Anxiety is a mood disorder characterized by nervousness, fear, apprehension, and worrying. Patients with anxiety disorders may report symptoms such as excessive worry, panic attacks, or avoidance of specific situations (e.g. social interactions, supermarkets). Treatment resistant anxiety (TRA; anxiety that has not resolved or improved despite adequate medication and psychotherapy) is relatively common, with approximately 30% of patients showing no response to treatment, and a further 30-40% of patients having a partial response (Brown 1996). No drug treatments are approved at present for TRA.

Autoinduction is the ability of a drug to induce enzymes that enhance its own metabolism, which may result in tolerance.

Phobias

Phobias are irrational fears that lead people to altogether avoid specific objects or situations that trigger intense anxiety. Phobias occur in several forms, for example, agoraphobia is the fear of being in any situation that might trigger a panic attack and from which escape might be difficult. Social Phobia or Social Anxiety Disorder is the fear of social situations and the interaction with other people, which can automatically bring on feelings of self-consciousness, judgment, evaluation, and criticism. It is the fear and anxiety of being judged and evaluated negatively by other people, leading to feelings of inadequacy, embarrassment, humiliation, and depression. Many of the physical symptoms that accompany panic attacks—such as sweating, racing heart, and trembling—also occur with phobias.

Phobias include specific phobias and complex phobias. Specific phobia is an anxiety disorder of which the essential feature is a persistent fear of a circumscribed stimulus, which may be an object or situation, other than fear of having a panic attack or of humiliation or embarrassment in social situations (which falls under social phobia). Examples include phobias of flying, heights, animals, injections, and blood. Simple phobias may be referred to as "specific" phobias. Exposure to the phobic stimulus will almost invariably lead to an immediate anxiety response. Social phobia is one type of complex phobia, and is characterized by the persistent fear of social or performance situations in which embarrassment may occur.

In DSM-5 (The Diagnostic and Statistical Manual of Mental Disorders (5th ed.; DSM-5; American Psychiatric Association, 2013), phobic disorders are anxiety states associated with intense fear or anxiety of situations or objects, and avoidance of those situations/objects. Phobic disorders have been subdivided into complex phobias (e.g. social anxiety disorder and agoraphobia), and simple or specific phobias (e.g. fear of heights, spiders, flying, blood). Specific phobias are common, with a 12 month prevalence of 7.3% and lifetime prevalence of 10.8% (NZ Mental Health Survey). In contrast to complex phobias, there are few treatment options for specific phobias. Psychological therapies such as systematic desensitization and cognitive behaviour therapy may be effective. There are few medication trials in patients with specific phobias, and no drugs have regulatory approval for this indication.

A recent analysis of Fear Questionnaire (Marks and Mathews) subscale data in 24 patients with treatment refractory anxiety showed that single subcutaneous doses of ketamine 0.25-1 mg/kg reduced ratings of the specific phobia Blood Phobia subscale in a dose-dependent manner (Glue unsubmitted manuscript). There was a positive dose-response relationship identified between FQBI scores at 2 hours and concentrations of ketamine (FIG. 2A) and norketamine at 2 hours (FIG. 2B); specifically lower scores were associated with higher drug concentrations. Compared with ketamine, there was a greater $R^2$ value for an exponential decline curve for the 2 hour norketamine concentrations and FQBI scores, which could support a greater role for norketamine in this clinical effect.

These improvements were maintained during a 3-month maintenance treatment phase. Ketamine appears to have broad anti-anxiety and antidepressant effects, and we have hypothesized that it may be working via an effect on neuroticism, a personality trait associated with internalizing disorders including specific phobia (Glue 2018).

The present invention may affect the somatic (e.g., peripheral and visceral) symptoms as well as the psychic (cognitive and emotional) symptoms of phobic disorders.

The invention provides a method of treating and/or preventing DSM-5 Specific Phobia wherein the DSM-5 Specific Phobia is selected from the group consisting of, for example, environmental phobia, animal phobia, situational phobia, bodily phobia, and combinations thereof. In certain embodiments, the environmental phobia is selected from the group consisting of, for example, fear of germs, deep water, heights, other environmental phobias, and combinations thereof. In certain embodiments, the animal phobia is selected from the group consisting of, for example, fear of dogs, spiders, snakes, other animal phobias, and combinations thereof. In certain embodiments, the situational phobia is selected from the group consisting of, for example, fear of flying in an aeroplane, visiting the dentist, other situational phobias, and combinations thereof. In certain embodiments, the bodily phobia is selected from the group consisting of, for example, fear of blood exposure, other bodily phobias, and combinations thereof.

The data presented in this application were based on subcutaneous dosing. However published studies have identified that the antidepressant response to ketamine is independent of route of administration—that is, clinically relevant improvements in mood are seen after intravenous, subcutaneous and intramuscular dosing (Loo 2016), oral dosing with liquid formulations (Schoevers 2016) and sustained release oral formulations such as R-107 (Douglas patent appl), and intranasal dosing (Daly 2018).

Given ketamine's broad antidepressant and anxiolytic effects, the effects of ketamine on anxiety associated with specific phobia will be evident via other methods of dosing, including oral dosing, and including extended and/or controlled release oral dosing and/or maintenance therapy dosing regimens.

Active Agent

The pharmaceutical composition of the the invention may comprise an active agent, selected from the group consisting of, for example, ketamine, norketamine, pharmaceutically acceptable salts thereof, and combinations thereof "Ketamine" as used herein is understood to comprise the compound of formula (I)

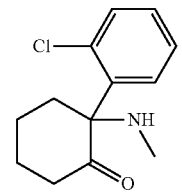 [SMILES: CNC1(c2ccccc2Cl)CCCCC1=O]

having the IUPAC name 2-(2-chlorophenyl)-2-(methylamino)cyclohexan-1-one. Accordingly, ketamine comprises the R and S enantiomers as well as pharmaceutically acceptable salts or solvates thereof. In one embodiment, ketamine is (R)-ketamine or pharmaceutically acceptable salts or solvates thereof. In another embodiment, ketamine is (S)-ketamine or pharmaceutically acceptable salts or solvates thereof. In a further embodiment, ketamine is a racemate of (S)-ketamine and (R)-ketamine or pharmaceutically acceptable salts or solvates thereof, or any mixture of (S)-ketamine and (R)-ketamine or pharmaceutically acceptable salts or solvates thereof. Ketamine can preferably comprise the pharmaceutically acceptable acid addition salts thereof. The acids which are used to prepare the pharmaceutically acceptable acid addition salts are preferably those which form non-toxic acid addition salts, i.e. salts containing pharmacologically acceptable anions, such as chloride, bromide, iodide, nitrate, sulfate, bisulfate, phosphate, acid phosphate, acetate, lactate, citrate, (D,L)- and L-tartrate, (D,L)- and L-malate, bitartrate, succinate, maleate, fumarate, gluconate, saccharate and benzoate. A preferred salt is the hydrochloride of ketamine.

Ketamine as used herein can also comprise its metabolites. The metabolite is norketamine or dehydronorketamine, preferably norketamine. Norketamine has the IUPAC name 2-amino-2-(2-chlorophenyl)cyclohexan-1-one of formula (II)

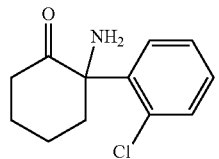 [SMILES: NC1(c2ccccc2Cl)CCCCC1=O]

and is obtained from ketamine through N-demethylation. Norketamine can be provided as (R)-norketamine or pharmaceutically acceptable salts or solvates thereof, or (S)-norketamine or pharmaceutically acceptable salts or solvates thereof, racemate of (5)-norketamine and (R)-norketamine or pharmaceutically acceptable salts or solvates thereof, or any mixture of (S)-norketamine and (R)-norketamine or pharmaceutically acceptable salts or solvates thereof.

In exemplary embodiments, formulations of the invention may comprise active agent at a concentration of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%. In exemplary embodiments, formulations of the invention may comprise active agent at a concentration of about 1 to 20%, of about 5% to 25%, about 10% to about 20%, or about 15% to about 18%.

Combination Therapy

Methods and compositions of treating and/or preventing a condition in a subject are provided according to embodiments of the present invention which include administering, in combination, a compound of the invention as set forth herein and at least one additional therapy, such as a therapeutic agent selected from the group consisting of at least one anti-anxiety drug, at least one anti-depressant drug, at least one neuroleptic medication, at least one mood stabilizer drug, at least one antipsychotic drug, at least one hypnotic, and combinations thereof. In exemplary embodiments, the active agent is administered in combination with or concurrently with another therapeutic intervention to enhance the efficacy thereof. Examples of other therapeutic interventions include, but are not limited to, counseling, psychotherapy, cognitive therapy or the like, electroconvulsive therapy, hydrotherapy, hyperbaric oxygen therapy, electrotherapy and electrical stimulation, transcutaneous electrical nerve stimulation or "TENS" (e.g., for the treatment of pain such as neuropathic pain), deep brain stimulation (e.g., for the treatment of pain such as neuropathic pain, Parkinson's disease, tremor, dystonia, etc.), vagus nerve stimulation and/or transcranial magnetic stimulation, etc.

In exemplary embodiments, at least one anti-anxiety drug is alprazolam, bromazepam, diazepam, lorazepam, clonazepam, temazepam, oxazepam, flunitrazepam, triazolam, chlordiazepoxide, flurazepam, estazolam, nitrazepam, and pharmaceutically acceptable salts, isomers, and mixtures thereof. Further examples of anxiolytic drugs include, but are not limited to, benzodiazepines (e.g., alprazolam, bromazepam (LEXOTAN), chlordiazepoxide (LIBRIUM), clobazam, clonazepam, clorazepate, diazepam, midazolam, lorazepam, nitrazepam, nimetazepam, estazolam, flunitrazepam, oxazepam (Serax), temazepam (RESTORIL, NORMISON, PLANUM, TENOX, and TEMAZE), triazolam, serotonin 1A agonists (e.g., buspirone (BUSPAR)), barbiturates (e.g., amobarbital (amytal sodium), pentobarbital (NEMBUTAL), secobarbital (SECONAL), phenobarbital, methohexital, thiopental, methylphenobarbital, metharbital, barbexaclone), hydroxyzine, cannabidiol, and herbal treatments. (e.g., valerian, kava (Kava Kava), chamomile, Kratom, Blue Lotus extracts, *Sceletium tortuosum* (kanna) and *Bacopa monniera*).

In exemplary embodiments, at least one anti-depressant drug is citalopram, escitalopram oxalate, fluoxetine, fluvoxamine, paroxetine, sertraline, dapoxetine; venlafaxine and duloxetine; harmaline, iproniazid, isocarboxazid, nialamide, pargyline, phenelzine, selegiline, toloxatone, tranylcypromine, brofaromine, moclobemide; amitriptyline, amoxapine, butriptyline, clomipramine, desipramine, dibenzepin, dothiepin, doxepin, imipramine, iprindole, lofepramine, melitracen, nortriptyline, opipramol, protriptyline, trimipramine; maprotiline, mianserin, nefazodone, trazodone, and pharmaceutically acceptable salts, isomers, and combinations thereof. Anti-depressant medications include synthesized chemical compounds as well as naturally occurring or herbal remedies such as St. John's Wort.

Herbal antidepressants may include, for example, St John's Wort; kava kava; echinacea; saw palmetto; holy basil; valerian; milk thistle; Siberian ginseng; Korean ginseng; ashwagandha root; nettle; Ginkgo biloba; gotu kola; ginkgo/gotu kola supreme; astragalus; goldenseal; dong quai; ginseng; St. John's wort supreme; echinacea; bilberry; green tea; hawthorne; ginger, gingko, turmeric; boswellia serata; black cohosh; cats claw; catnip; chamomile; dandelion; chaste tree berry; black elderberry; feverfew; garlic; horse chestnut; licorice; red clover blossom and leaf rhodiola rusa; coleus forskohlii; Passion Flower; eyebright; yohimbe; blueberry plant; black pepper plant; *Hydrocotyle asiatica*; astragalus; valerian poppy root and grape seed; vervain; echinacea ang root; Skull Cap; serenity elixir; and combinations thereof.

Examples of antidepressants include, but are not limited to, selective serotonin reuptake inhibitors (SSRIs) (e.g., fluoxetine (PROZAC), paroxetine (PAXIL, SEROXAT), escitalopram (LEXAPRO, ESIPRAM), citalopram (CELEXA), and sertraline (ZOLOFT)), serotonin-norepinephrine reuptake inhibitors (SNRIs) (e.g., venlafaxine (EFFEXOR), and duloxetine (CYMBALTA)), noradrenergic and specific serotonergic antidepressants (NASSAs) (e.g., mirtazapine (AVANZA, ZISPIN, REMERON)), norepinephrine (noradrenaline) reuptake inhibitors (NRIs) (e.g., reboxetine (EDRONAX)), norepinephrine-dopamine reuptake inhibitors (e.g., bupropion (WELLBUTRIN, ZYBAN)), tricyclic antidepressants (TCAs) (e.g., amitriptyline and desipramine), monoamine oxidase inhibitor (MAOIs) (e.g., phenelzine (NARDIL), moclobemide (MANERIX), selegiline), and augmentor drugs (e.g., tryptophan (TRYPTAN) and buspirone (BUSPAR)).

In exemplary embodiments, at least one neuroleptic drug is haloperidol (HALDOL), droperidol, benperidol, triperidol, melperone, lenperone, azaperone, domperidone, risperidone, chlorpromazine, fluphenazine, perphenazine, prochlorperazine, thioridazine, trifluoperazine, mesoridazine, periciazine, promazine, triflupromazine, levomepromazine, promethazine, pimozide, cyamemazine, chlorprothixene, clopenthixol, flupenthixol, thiothixene, zuclopenthixol, clozapine, olanzapine, risperidone, quetiapine, ziprasidone, amisulpride, asenapine, paliperidone, iloperidone, zotepine, sertindole, lurasidone, aripiprazole, and pharmaceutically acceptable salts, isomers, and combinations thereof, In exemplary embodiments, at least one mood stabilizer drugs includes, but is not limited to, Lithium carbonate, lithium orotate, lithium salt, Valproic acid (DEPAKENE), divalproex sodium (DEPAKOTE), sodium valproate (DEPACON), Lamotrigine (LAMICTAL), Carbamazepine (TEGRETOL), Gabapentin (NEURONTIN), Oxcarbazepine (TRILEPTAL), and Topiramate (TOPAMAX), and combinations thereof.

Examples of antipsychotic drugs include, but are not limited to, butyrophenones (e.g., haloperidol), phenothiazines (e.g., chlorpromazine (THORAZINE), fluphenazine (PROLIXIN), perphenazine (TRILAFON), prochlorperazine (COMPAZINE), thioridazine (MELLARIL), trifluoperazine (STELAZINE), mesoridazine (SERENTIL), promazine, triflupromazine (VESPRIN), levomepromazine (NOZINAN), promethazine (PHENERGAN)), thioxanthenes (e.g., chlorprothixene (TRUXAL), flupenthixol (DEPIXOL and FLUANXOL), thiothixene (NAVANE), zuclopenthixol (CLOPIXOL & ACUPHASE)), clozapine, olanzapine, risperidone (RISPERDAL), quetiapine (SEROQUEL), ziprasidone (GEODON), amisulpride (SOLIAN), paliperidone (INVEGA), dopamine, bifeprunox, norclozapine (ACP-104), Aripiprazole (ABILIFY), tetrabenazine (XENAZINE), and cannabidiol and pharmaceutically acceptable salts, isomers, and combinations thereof.

Examples of hypnotics include, but are not limited to, barbiturates, opioids, benzodiazepines (e.g., alprazolam, bromazepam (Lexotan), chlordiazepoxide (Librium), clobazam, clonazepam, clorazepate, diazepam, midazolam, lorazepam, nitrazepam, nimetazepam, estazolam, flunitrazepam, oxazepam (SERAX), temazepam (RESTORIL, NORMISON, PLANUM, TENOX, and TEMAZE), triazolam), non-benzodiazepines (e.g., ZOLPIDEM, ZALEPLON, ZOPICLONE, ESZOPICLONE), antihistamines (e.g., diphenhydramine, doxylamine, hydroxyzine, promethazine), gamma-hydroxybutyric acid (Xyrem), Glutethimide, Chloral hydrate, Ethchlorvynol, Levomepromazine, Chlormethiazole, Melatonin, and Alcohol. Examples of sedatives include, but are not limited to, barbituates (e.g., amobarbital (Amytal), pentobarbital (Nembutal), secobarbital (Seconal), phenobarbital, methohexital, thiopental, methylphenobarbital, metharbital, barbexaclone), benzodiazepines (e.g., alprazolam, bromazepam (LEXOTAN), chlordiazepoxide (LIBRIUM), clobazam, clonazepam, clorazepate, diazepam, midazolam, lorazepam, nitrazepam, nimetazepam, estazolam, flunitrazepam, oxazepam (SERAX), temazepam (RESTORIL, NORMISON, PLANUM, TENOX, and TEMAZE), triazolam), and pharmaceutically acceptable salts, isomers, and combinations thereof. Examples further include Herbal sedatives (e.g., ashwagandha, catnip, kava (*Piper methysticum*), mandrake, marijuana, valerian), solvent sedatives (e.g., chloral hydrate (NOCTEC), diethyl ether (Ether), ethyl alcohol (alcoholic beverage), methyl trichloride (chloroform)), nonbenzodiazepine sedatives (e.g., eszopiclone (LUNESTA), zaleplon (SONATA), zolpidem (AMBIEN), zopiclone (IMOVANE, ZIMOVANE)), clomethiazole, gamma-hydroxybutyrate (GHB), thalidomide, ethchlorvynol (PLACIDYL), glutethimide (DORIDEN), ketamine (KETALAR, KETASET), methaqualone (SOPOR, QUAALUDE), methyprylon (NOLUDAR), and ramelteon (ROZEREM).

Examples of alpha-2-delta ligand include gabapentin, pregabalin, 3-methylgabapentin, (1alpha,3 alpha,5alpha)(3-amino-methyl-bicyclo[3.2.0]hept-3-yl)-acetic acid, (3S, 5R)-3 aminomethyl-5 methyl-heptanoic acid, (3S,5R)-3 amino-5 methyl-heptanoic acid, (3S,5R)-3 amino-5 methyl-octanoic acid, (2S,4S)-4-(3-chlorophenoxy)proline, (2S, 4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4 S)-(1-aminomethyl-3,4-dimethyl-cyclopentyl)-acetic acid, (3S,5R)-3 aminomethyl-5 methyl-octanoic acid, (3S,5R)-3 amino-5 methyl-nonanoic acid, (3S,5R)-3 amino-5 methyl-octanoic acid, (3R,4R,5R)-3-amino-4,5-dimethyl-heptanoic acid and (3R,4R,5R)-3-amino-4,5-dimethyl-octanoic acid, and combinations thereof.

Examples of serotonin 1a partial agonist include buspirone, gepirone, eltoprazine, or tandospirone, pharmaceutically acceptable salts, isomers, and combinations thereof.

Examples of antiadrenergic agents include clonidine, prazosin, propranolol, fuanfacine, methyldopa, guanabenz; doxazosin, prazosin, terazosin, silodosin, alfuzosin, tamsulosin, dutasertide/tamsulosin, guanadrel, mecemylamine, guanethidine, pharmaceutically acceptable salts, isomers, and combinations thereof.

Examples of benzodiazepine agents include alprazolam, bromazepam (LEXOTAN), chlordiazepoxide (LIBRIUM), clobazam, clonazepam, clorazepate, diazepam, midazolam, lorazepam, nitrazepam, nimetazepam, estazolam, flunitrazepam, oxazepam (SERAX), temazepam (RESTORIL, NORMISON, PLANUM, TENOX, and TEMAZE), triazolam, pharmaceutically acceptable salts, isomers, and combinations thereof.

The agents are administered in therapeutically effective amounts. In certain embodiments the agents are administered in the same dosage form. In certain embodiments the therapeutic agents are administered separately.

Pharmacokinetics

The formulation of the invention provides extended release of ketamine of, for example, over 4 hours, over 5 hours, over 6 hours, over 7 hours, over 8 hours, over 9 hours, over 10 hours, or more. Elimination half-life estimates for ketamine and norketamine for the formulation as set forth herein are much longer that previously reported for immediate release tablet formulations (e.g. 8 hr vs<2 hr; Yanagihara 2002)

Figure 10:
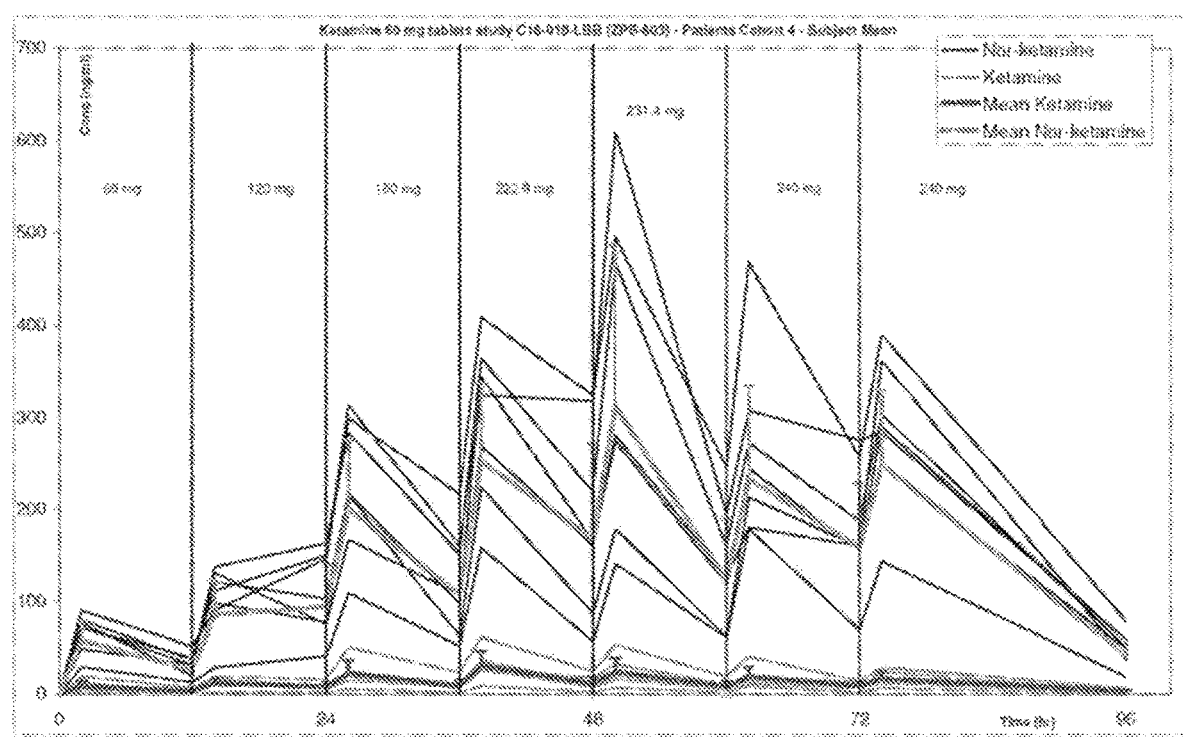
FIG. 10 is a chart showing individual and mean concentration-time profiles of ketamine and norketamine, Cohort 4. Mean dose administered at each 12 hour interval is shown above the concentration-time plots.

There is evidence that the formulations of the invention provide for autoinduction (FIG. 10). This appears to have stabilized after 3-4 days of repeat dosing. There is no prior human data on this.

There is evidence for the formulations of the invention that over 90% of the absorbed drug is present as norketamine rather than ketamine. In the patient cohort (cohort 4) there were improvements in depression and anxiety despite the major measurable drug present being norketamine. There has been much discussion in the scientific literature about whether ketamine or a metabolite are important in producing improvements in mood after dosing with ketamine. Zanos 2016 and Zarate 2017 highlight ketamine's metabolite, 6-hydroxy norketamine as important. The inventors have surprisingly found that norketamine itself is important in the tablet's therapeutic effects. This is in contrast to a previous report which presented data as combined ketamine and norketamine, rather than separately, and did not report on the importance of norketamine to the therapeutic effect. (See WO 2015/031410).

Figure 2A:
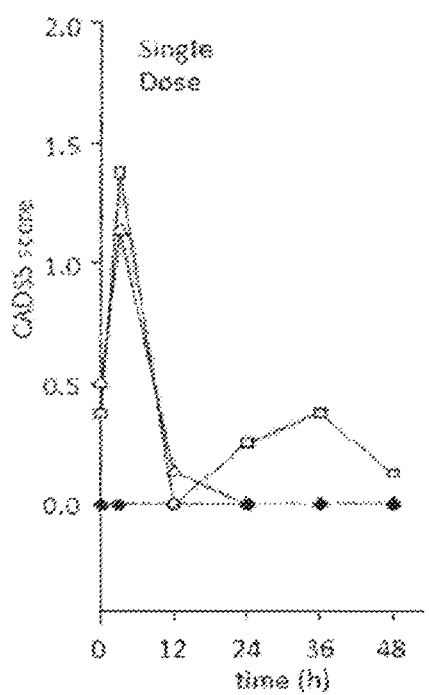
FIG. 2A is a chart showing the mean dissociation scale scores, using the Clinician-Administered Dissociative States Scale (CADSS) after a single dose of the sustained release tablet.
Figure 2B:
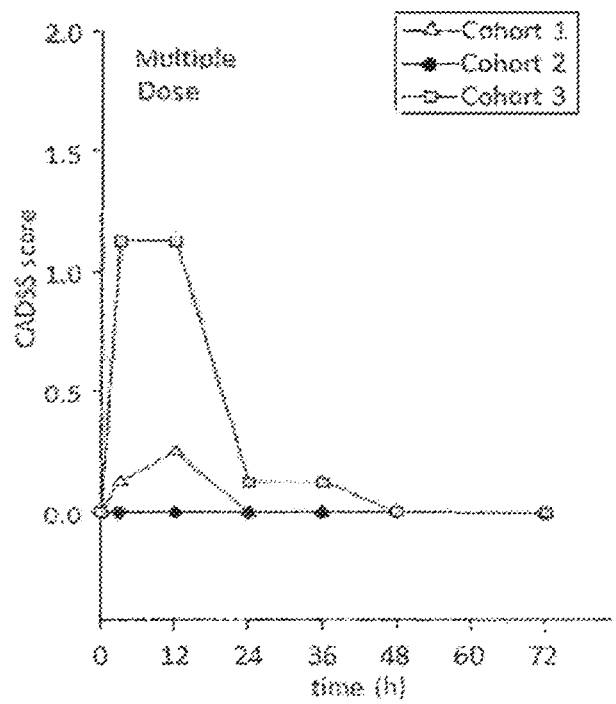
FIG. 2B is a chart showing mean CADS S scores after multiple doses of the tablet, Cohorts 1-3.

The oral formulation as set forth herein has no dissociative side effects after 60-120 mg doses, and minimal dissociative side effects at 240 mg (FIGS. 2A and 2B). This contrasts markedly with injected ketamine by any route of administration (e.g. Loo 2016), where there are marked dissociative symptoms for up to 60 minutes after dosing.

There is evidence that the formulations of the invention are efficacious in improving both depressed and anxious mood, with improved tolerability compared with injected ketamine. For example, a leading research group has highlighted a finding that having a dissociative experience is critical to mood improvement in TRD. "Among the examined mediators of ketamine's antidepressant response, only dissociative side effects predicted a more robust and sustained antidepressant" (ncbi.nlm.nih.gov/pubmed/24679390). The inventors have found that improvement in depression scores occurs with no or minimal dissociation (see FIGS. 8 and 5A). This observation of improvement in depression scores in the absence of dissociation is novel and nonobvious.

The onset of improvement of anxiety symptoms in study 603 cohort 4 was more gradual (48 h) compared with 1-2 h for injected ketamine (FIG. 7), however the same overall magnitude of effect was observed as with injected drug in earlier treatment.

Furthermore, a safe and effective dose and dosing schedule have been identified in an open-label extension study for patients who completed the 603 study. Three of 4 patients with mixed anxiety/depressive disorders remained in remission on doses of 120 mg orally once or twice weekly.

Matrix Formulations

In certain embodiments, the present invention is directed to a process of preparing a solid oral extended release pharmaceutical dosage form, comprising at least the steps of:
  (a) combining:
    (1) at least one polyethylene oxide having, based on rheological measurements, an approximate molecular weight selected from the group consisting of at least about 1,000,000; at least about 2,000,000; at least about 3,000,000; at least about 4,000,000; at least about 5,000,000; at least about 6,000,000; at least about 6,000,000; at least about 7,000,000; and at least about 8,000,000; and
    (2) at least one active agent, to form a composition;
  (b) shaping the composition to form an extended release matrix formulation; and
  (c) curing said extended release matrix formulation comprising at least a curing step of subjecting the extended release matrix formulation to a temperature which is at least the softening temperature of said polyethylene oxide for a time period selected from the group consisting of at least about 1 minute, at least about 2 minutes, at least about 3 minutes, at least about 4 minutes, at least about 5 minutes, at least about 6 minutes, at least about 7 minutes, at least about 8 minutes, at least about 9 minutes, and at least about 10 minutes. Preferably, the curing is conducted at atmospheric pressure. In a preferred embodiment the dosage form is coated.

In certain embodiments the composition is shaped in step b) to form an extended release matrix formulation in the form of tablet. For shaping the extended release matrix formulation in the form of tablet a direct compression process can be used. Direct compression is an efficient and simple process for shaping tablets by avoiding process steps like wet granulation. However, any other process for manufacturing tablets as known in the art may be used, such as wet granulation and subsequent compression of the granules to form tablets.

In one embodiment, the curing of the extended release matrix formulation in step c) comprises at least a curing step wherein the high molecular weight polyethylene oxide in the extended release matrix formulation at least partially melts. For example, at least about 20% or at least about 30% of the high molecular weight polyethylene oxide in the extended release matrix formulation melts. Preferably, at least about 40% or at least about 50%, more preferably at least about 60%, at least about 75% or at least about 90% of the high molecular weight polyethylene oxide in the extended release matrix formulation melts. In a preferred embodiment, about 100% of the high molecular weight polyethylene oxide melts.

In other embodiments, the curing of the extended release matrix formulation in step c) comprises at least a curing step wherein the extended release matrix formulation is subjected to an elevated temperature for a certain period of time. In such embodiments, the temperature employed in step c), i.e. the curing temperature, is at least as high as the softening temperature of the high molecular weight polyethylene oxide. Without wanting to be bound to any theory it is believed that the curing at a temperature that is at least as high as the softening temperature of the high molecular weight polyethylene oxide causes the polyethylene oxide particles to at least adhere to each other or even to fuse. According to some embodiments the curing temperature is at least about 60° C. or at least about 62° C., or ranges from about 62° C., to about 90° C., or from about 62° C. to about 85° C. or from about 62° C. to about 80° C. or from about 65° C. to about 90° C. or from about 65° C. to about 85° C. or from about 65° C. to about 80° C. The curing temperature preferably ranges from about 68° C. to about 90° C. or from about 68° C. to about 85° C. or from about 68° C. to about 80° C., more preferably from about 70° C. to about 90° C. or from about 70° C. to about 85° C. or from about 70° C. to about 80° C., most preferably from about 75° C. to about 90° C. or from about 75° C. to about 85° C. or from about 72° C. to about 80° C., or from about 70° C. to about 75° C. The curing temperature may be at least about 60° C. or at least about 62° C., but less than about 90° C. or less than about 80° C. Preferably, it is in the range of from about 62° C. to about 75° C., in particular from about 68° C. to about 75° C. Preferably, the curing temperature is at least as high as the lower limit of the softening temperature range of the high molecular weight polyethylene oxide or at least about 62° C. or at least about 68° C. More preferably, the curing temperature is within the softening temperature range of the high molecular weight polyethylene oxide or at least about 70° C. Even more preferably, the curing temperature is at least as high as the upper limit of the softening temperature range of the high molecular weight polyethylene oxide or at least about 72° C. In an alternative embodiment, the curing temperature is higher than the upper limit of the softening temperature range of the high molecular weight polyethylene oxide, for example the curing temperature is at least about 75° C. or at least about 80° C.

The curing time may vary from about 1 minute to about 24 hours or from about 5 minutes to about 20 hours or from about 10 minutes to about 15 hours or from about 15 minutes to about 10 hours or from about 30 minutes to about 5 hours depending on the specific composition and on the formulation and the curing temperature. The parameter of the composition, the curing time and the curing temperature are chosen to achieve the tamper resistance as described herein. According to certain embodiments the curing time varies from about 15 minutes to about 30 minutes.

In certain embodiments of the present invention, the sustained release formulation may be achieved via a matrix optionally having a controlled release coating as set forth herein. The present invention may also utilize a sustained release matrix that affords in-vitro dissolution rates of the API within desired ranges and releases the API in a pH-dependent or pH-independent manner.

A non-limiting list of suitable sustained-release materials which may be included in a sustained-release matrix according to the invention includes hydrophilic and/or hydrophobic materials, such as gums, cellulose ethers, acrylic resins, protein derived materials, waxes, shellac, and oils such as hydrogenated castor oil and hydrogenated vegetable oil. However, any pharmaceutically acceptable hydrophobic or hydrophilic sustained-release material which is capable of imparting sustained-release of the API may be used in accordance with the present invention. Preferred sustained-release polymers include alkylcelluloses such as ethylcellulose, acrylic and methacrylic acid polymers and copolymers; and cellulose ethers, especially hydroxyalkylcelluloses (especially hydroxypropylmethylcellulose) and carboxyalkylcelluloses. Preferred acrylic and methacrylic acid polymers and copolymers include methyl methacrylate, methyl methacrylate copolymers, ethoxyethyl methacrylates, ethyl acrylate, trimethyl ammonioethyl methacrylate, cyanoethyl methacrylate, aminoalkyl methacrylate copolymer, poly(acrylic acid), poly(methacrylic acid), methacrylic acid alkylamine copolymer, poly(methylmethacrylate), poly(methacrylic acid) (anhydride), polymethacrylate, polyacrylamide, poly(methacrylic acid anhydride), and glycidyl methacrylate copolymers. Certain preferred embodiments utilize mixtures of any of the foregoing sustained-release materials in the matrix of the invention. The matrix also may include a binder.

In addition to the above ingredients, a sustained-release matrix may also contain suitable quantities of other materials, e.g., diluents, lubricants, binders, granulating aids and glidants that are conventional in the pharmaceutical art.

A sustained-release matrix can be prepared by, e.g., melt-granulation or melt-extrusion techniques. Generally, melt-granulation techniques involve melting a normally solid hydrophobic binder material, e.g., a wax, and incorporating a powdered drug therein. To obtain a sustained release dosage form, it may be necessary to incorporate a hydrophobic sustained-release material, e.g., ethylcellulose or a water-insoluble acrylic polymer, into the molten wax hydrophobic binder material.

The additional hydrophobic binder material may comprise one or more water-insoluble wax-like thermoplastic substances possibly mixed with one or more wax-like thermoplastic substances being less hydrophobic than said one or more water-insoluble wax-like substances. In order to achieve sustained release, the individual wax-like substances in the formulation should be substantially non-degradable and insoluble in gastrointestinal fluids during the initial release phases. Useful water-insoluble wax-like binder substances may be those with a water-solubility that is lower than about 1:5,000 (w/w).

The preparation of a suitable melt-extruded matrix according to the present invention may, for example, include the steps of blending the API with a sustained release material and preferably a binder material to obtain a homogeneous mixture. The homogeneous mixture is then heated to a temperature sufficient to at least soften the mixture sufficiently to extrude the same. The resulting homogeneous mixture is then extruded, e.g., using a twin-screw extruder, to form strands. The extrudate is preferably cooled and cut into multiparticulates by any means known in the art. The matrix multiparticulates are then divided into unit doses. The extrudate preferably has a diameter of from about 0.1 to about 5 mm and provides sustained release of the active agent or pharmaceutically acceptable salt thereof for a time period of at least about 24 hours.

An optional process for preparing the melt extruded formulations of the present invention includes directly metering into an extruder a hydrophobic sustained release material, the API, and an optional binder material; heating the homogenous mixture; extruding the homogenous mixture to thereby form strands; cooling the strands containing the homogeneous mixture; cutting the strands into matrix multiparticulates having a size from about 0.1 mm to about 12 mm; and dividing said particles into unit doses. In this aspect of the invention, a relatively continuous manufacturing procedure is realized.

Plasticizers, such as those described above, may be included in melt-extruded matrices. The plasticizer is preferably included as from about 0.1 to about 30% by weight of the matrix. Other pharmaceutical excipients, e.g., talc, mono or poly saccharides, lubricants and the like may be included in the sustained release matrices of the present invention as desired. The amounts included will depend upon the desired characteristic to be achieved.

The diameter of the extruder aperture or exit port can be adjusted to vary the thickness of the extruded strands. Furthermore, the exit part of the extruder need not be round; it can be oblong, rectangular, etc. The exiting strands can be reduced to particles using a hot wire cutter, guillotine, etc.

A melt extruded matrix multiparticulate system can be, for example, in the form of granules, spheroids or pellets depending upon the extruder exit orifice. For purposes of the present invention, the terms "melt-extruded matrix multiparticulate(s)" and "melt-extruded matrix multiparticulate system(s)" and "melt-extruded matrix particles" shall refer to a plurality of units, preferably within a range of similar size and/or shape and containing one or more active agents and one or more excipients, preferably including a hydrophobic sustained release material as described herein. Preferably the melt-extruded matrix multiparticulates will be of a range of from about 0.1 to about 12 mm in length and have a diameter of from about 0.1 to about 5 mm. In addition, it is to be understood that the melt-extruded matrix multiparticulates can be any geometrical shape within this size range. In certain embodiments, the extrudate may simply be cut into desired lengths and divided into unit doses of the therapeutically active agent without the need of a spheronization step.

In one preferred embodiment, oral dosage forms are prepared that include an effective amount of melt-extruded matrix multiparticulates within a capsule. For example, a plurality of the melt-extruded matrix multiparticulates may be placed in a gelatin capsule in an amount sufficient to provide an effective sustained release dose when ingested and contacted by gastrointestinal fluid.

In another embodiment, a suitable amount of the multiparticulate extrudate is compressed into an oral tablet using conventional tableting equipment using standard techniques. Techniques and compositions for making tablets (compressed and molded), capsules (hard and soft gelatin) and pills are described in Remington's Pharmaceutical Sciences, (Arthur Osol, editor), 1553-1593 (1980).

In addition to the above ingredients, the spheroids, granules, or matrix multiparticulates may also contain suitable quantities of other materials, e.g., diluents, lubricants, binders, granulating aids, and glidants that are conventional in the pharmaceutical art in amounts up to about 50% by weight of the formulation if desired. The quantities of these additional materials will be sufficient to provide the desired effect to the desired formulation.

In one embodiment, at least one active agent in solubility-improved form is incorporated into an erodible or non-erodible polymeric matrix controlled release formulation. By an erodible matrix is meant aqueous-erodible or water-swellable or aqueous-soluble in the sense of being either erodible or swellable or dissolvable in pure water or requiring the presence of an acid or base to ionize the polymeric matrix sufficiently to cause erosion or dissolution. When contacted with the aqueous environment of use, the erodible polymeric matrix imbibes water and forms an aqueous-swollen gel or "matrix" that entraps the solubility-improved form of the active agent. The aqueous-swollen matrix gradually erodes, swells, disintegrates or dissolves in the environment of use, thereby controlling the release of the active agent to the environment of use. The erodible polymeric matrix into which the active agent is incorporated may generally be described as a set of excipients that are mixed with the solubility-improved form following its formation that, when contacted with the aqueous environment of use imbibes water and forms a water-swollen gel or "matrix" that entraps the drug form. Drug release may occur by a variety of mechanisms: the matrix may disintegrate or dissolve from around particles or granules of the drug in solubility-improved form; or the drug may dissolve in the imbibed aqueous solution and diffuse from the tablet, beads or granules of the formulation. A key ingredient of this water-swollen matrix is the water-swellable, erodible, or soluble polymer, which may generally be described as an osmopolymer, hydrogel or water-swellable polymer. Such polymers may be linear, branched, or crosslinked. They may be homopolymers or copolymers. Although they may be synthetic polymers derived from vinyl, acrylate, methacrylate, urethane, ester and oxide monomers, they are most preferably derivatives of naturally occurring polymers such as polysaccharides or proteins.

Such materials include naturally occurring polysaccharides such as chitin, chitosan, dextran and pullulan; gum agar, gum arabic, gum karaya, locust bean gum, gum tragacanth, carrageenans, gum ghatti, guar gum, xanthan gum and scleroglucan; starches such as dextrin and maltodextrin; hydrophilic colloids such as pectin; phosphatides such as lecithin; alginates such as ammonium alginate, sodium, potassium or calcium alginate, propylene glycol alginate; gelatin; collagen; and cellulosics. By "cellulosics" is meant a cellulose polymer that has been modified by reaction of at least a portion of the hydroxyl groups on the saccharide repeat units with a compound to form an ester-linked or an ether-linked substituent. For example, the cellulosic ethyl cellulose has an ether linked ethyl substituent attached to the saccharide repeat unit, while the cellulosic cellulose acetate has an ester linked acetate substituent.

A preferred class of cellulosics for the erodible matrix comprises aqueous-soluble and aqueous-erodible cellulosics such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC). A particularly preferred class of such cellulosics comprises various grades of low viscosity (MW less than or equal to 50,000 daltons) and high viscosity (MW greater than 50,000 daltons) HPMC. Commercially available low viscosity HPMC polymers include the Dow METHOCEL series E5, E15LV, E50LV and K100LY, while high viscosity HPMC polymers include E4MCR, E10MCR, K4M, K15M and K100M; especially preferred in this group are the METHOCEL K series. Other commercially available types of HPMC include the Shin Etsu METOLOSE 90SH series.

Although the primary role of the erodible matrix material is to control the rate of release of the active agent in solubility-improved form to the environment of use, the inventors have found that the choice of matrix material can have a large effect on the maximum drug concentration attained by the formulation as well as the maintenance of a high drug concentration. In one embodiment, the matrix material is a concentration-enhancing polymer, as defined herein below.

Other materials useful as the erodible matrix material include, but are not limited to, pullulan, polyvinyl pyrrolidone, polyvinyl alcohol, polyvinyl acetate, glycerol fatty acid esters, polyacrylamide, polyacrylic acid, copolymers of ethacrylic acid or methacrylic acid (EUDRAGIT®, Rohm America, Inc., Piscataway, N.J.) and other acrylic acid derivatives such as homopolymers and copolymers of butylmethacrylate, methylmethacrylate, ethylmethacrylate, ethylacrylate, (2-dimethylaminoethyl)methacrylate, and (trimethylaminoethyl) methacrylate chloride.

The erodible matrix polymer may contain a wide variety of the same types of additives and excipients known in the pharmaceutical arts, including osmopolymers, osmagens, solubility-enhancing or -retarding agents and excipients that promote stability or processing of the formulation.

The formulation may comprise an excipient that is a swellable material such as a hydrogel in amounts that can swell and expand. Examples of swellable materials include polyethylene oxide, hydrophilic polymers that are lightly cross-linked, such cross-links being formed by covalent or ionic bond, which interact with water and aqueous biological fluids and swell or expand to some equilibrium state. Swellable materials such as hydrogels exhibit the ability to swell in water and retain a significant fraction of water within its structure, and when cross-linked they will not dissolve in the water. Swellable polymers can swell or expand to a very high degree, exhibiting a 2 to 50 fold volume increase. Specific examples of hydrophilic polymeric materials include poly(hydroxyalkyl methacrylate), poly(N-vinyl-2-pyrrolidone), anionic and cationic hydrogels, polyelectrolyte complexes, poly(vinyl alcohol) having a low acetate residual and cross-linked with glyoxal, formaldehyde, or glutaraldehyde, methyl cellulose cross-linked with dialdehyde, a mixture of cross-linked agar and carboxymethyl cellulose, a water insoluble, water-swellable copolymer produced by forming a dispersion of finely divided copolymer of maleic anhydride with styrene, ethylene, propylene, butylene, or isobutylene cross-linked with from 0.001 to about 0.5 moles of a polyunsaturated cross-linking agent per mole of maleic anhydride in the copolymer, water-swellable polymers of N-vinyl lactams, cross-linked polyethylene oxides, and the like. Other examples of swellable materials include hydrogels exhibiting a cross-linking of 0.05 to 60%, hydrophilic hydrogels known as Carbopol acidic carboxy polymer, Cyanamer™ polyacrylamides, cross-linked water-swellable indene-maleic anhydride polymers, Good-Rite™ polyacrylic acid, starch graft copolymers, Aqua-Keeps.™ acrylate polymer, diester cross-linked polyglucan, and the like.

The formulations may comprise additives such as polyethylene oxide polymers, polyethylene glycol polymers, cellulose ether polymers, cellulose ester polymers, homo- and copolymers of acrylic acid cross-linked with a polyalkenyl polyether, poly(meth)acrylates, homopolyers (e.g., polymers of acrylic acid crosslinked with allyl sucrose or allyl pentaerythritol), copolymers (e.g., polymers of acrylic acid and $C_{10}$-$C_{30}$ alkyl acrylate crosslinked with allyl pentaerythritol), interpolymers (e.g., a homopolymer or copolymer that contains a block copolymer of polyethylene glycol and a long chain alkyl acid ester), disintegrants, ion exchange resins, polymers reactive to intestinal bacterial flora (e.g., polysaccharides such as guar gum, inulin obtained from plant or chitosan and chondrotin sulphate obtained from animals or alginates from algae or dextran from microbial origin) and pharmaceutical resins.

Polyalkylene Oxides

The pharmaceutical composition of the invention may comprise at least one polyalkylene oxide having an average molecular weight of no more than about 300,000 may be a polyethylene oxide, a polymethylene oxide, a polypropylene oxide, or a copolymer thereof. In exemplary embodiments, the first polyalkylene oxide is a polyethylene oxide. In some embodiments, the polyalkylene oxide, which may be polyethylene oxide, has an average molecular weight of about 300,000. In other embodiments, the polyalkylene oxide, which may be polyethylene oxide, has an average molecular weight of about 200,000. In specific embodiments, the polyalkylene oxide, which may be polyethylene oxide, has an average molecular weight of about 100,000.

In exemplary embodiments, the pharmaceutical composition of the invention may comprise polyalkylene oxide having an average molecular weight of at least 1,000,000 may be a polyethylene oxide, a polymethylene oxide, a polypropylene oxide, or a copolymer thereof. In exemplary embodiments, the polyalkylene oxide is a polyethylene oxide. In some embodiments, the second polyalkylene oxide, which may be polyethylene oxide, has an average molecular weight of about 2,000,000. In other embodiments, the polyalkylene oxide, which may be polyethylene oxide, has an average molecular weight of about 4,000,000. In further embodiments, the second polyalkylene oxide, which may be polyethylene oxide, has an average molecular weight of about 5,000,000. In still other embodiments, the polyalkylene oxide, which may be polyethylene oxide, has an average molecular weight of about 7,000,000. In additional embodiments, the polyalkylene oxide, which may be polyethylene oxide, has an average molecular weight of about 8000,000. In other embodiments, the polyalkylene oxide, which may be polyethylene oxide, has an average molecular weight of about 15,000,000.

In exemplary embodiments, the polymer may be selected from the group comprising polyalkylene oxides, preferably polymethylene oxide, polyethylene oxide, polypropylene oxide; polyethylene, polypropylene, polyvinyl chloride, polycarbonate, polystyrene, polyacrylate, copolymers thereof, and mixtures of at least two of the stated polymers.

In exemplary embodiments, the polymer may be a water-soluble polymer for use either as a base polymer material or as a dissolution modifying agent such as polyethylene oxide (PEO), for example the brand name POLYOX® (Dow). It is recognized that the thermoplastic polymers may be used in varying molecular weights, such as 100K, 200K, 300K, 400K, 600K, 900K, 1000K, 2000K, 4000K, 5000K, 7000K and 8000K (K=1,000), and optionally combinations thereof. In a preferred embodiment, the PEO is a high molecular weight PEO. In a preferred embodiment, the PEO has a molecular weight of about 7,000,000. In a preferred embodiment, the PEO has a molecular weight between about 4,000,000 and 8,000,000. Examples of polyethylene oxide include POLYOX water soluble resin, which is listed in the NF and has approximate molecular weights which range from 100,000 to about 8,000,000. A preferred polyethylene oxide is POLYOX WSR-80, POLYOX WSR N-750, POLYOX WSR-205, POLYOX WSR-1105, POLYOX WSRN-12K, POLYOX WSRN-60K, WSR-301, WSR Coagulant, WSR-303, and combinations thereof.

The amount of polyalkylene oxide present in the pharmaceutical composition can and will vary and in general, the amount of the polyalkylene oxide present in the pharmaceutical composition may range from about 10% to about 95% by weight of the composition. In various embodiments, the amount of the polyalkylene oxide present in the pharmaceutical composition may range from about 20% to about 90%, from about 30% to about 80%, or from about 35% to about 70% by weight of the pharmaceutical composition. In various embodiments, the amount of the polyalkylene oxide present in the pharmaceutical composition may be about 50%, 55%, 60%, 65%, 70%, 75%, 80%, 85%, 90%, or 95%.

In the above described embodiments high molecular weight polyethylene oxide having, based on rheological measurements, an approximate molecular weight of from 2,000,000 to 15,000,000 or from 2,000,000 to 8,000,000 may be used. In particular polyethylene oxides having, based on rheological measurements, an approximate molecular weight of 2,000,000, 4,000,000, 7,000,000 or 8,000,000 may be used. In particular polyethylene oxides having, based on rheological measurements, an approximate molecular weight of 4,000,000, may be used.

In embodiments wherein the composition further comprises at least one low molecular weight polyethylene oxide is used polyethylene oxides having, based on rheological measurements, an approximate molecular weight of less than 1,000,000, such as polyethylene oxides having, based on rheological measurements, an approximate molecular weight of from 100,000 to 900,000 may be used. The addition of such low molecular weight polyethylene oxides may be used to specifically tailor the release rate such as enhance the release rate of a formulation that otherwise provides a release rate to slow for the specific purpose. In such embodiments at least one polyethylene oxide having, based on rheological measurements, an approximate molecular weight of 100,000 may be used.

In certain such embodiments the composition comprises at least one polyethylene oxide having, based on rheological measurements, an approximate molecular weight of at least 1,000,000 and at least one polyethylene oxide having, based on rheological measurements, an approximate molecular weight of less than 1,000,000, wherein the composition comprises at least about 10% (by wt) or at least about 20% (by wt) of the polyethylene oxide having, based on rheological measurements, an approximate molecular weight of less than 1,000,000. In certain such embodiments the curing temperature is less than about 80° C. or even less than about 77° C. In certain embodiments the overall content of polyethylene oxide in the composition is at least about 80% (by wt).

Lubricant

In exemplary embodiments, the pharmaceutical composition of the invention may include lubricants such as talc, calcium stearate, magnesium stearate, solid polyethylene glycols, sodium lauryl sulfate, and mixtures thereof and other tableting aids such a magnesium stearate and microcrystalline cellulose The pharmaceutical compositions disclosed herein may also further comprise at least one lubricant, which facilitates preparation of solid dosage forms of the pharmaceutical composition. Non-limiting examples of suitable lubricants include magnesium stearate, calcium stearate, zinc stearate, colloidal silicon dioxide, hydrogenated vegetable oils, sterotex, polyoxyethylene monostearate, polyethylene glycol, sodium stearyl fumarate, sodium benzoate, sodium lauryl sulfate, magnesium lauryl sulfate, and light mineral oil. In exemplary embodiments, the lubricant may be magnesium stearate.

In embodiments in which the lubricant is included in the pharmaceutical composition, the amount of the lubricant may range from about 0.1% to about 3% by weight of the pharmaceutical composition. In various embodiments, the amount of the lubricant may range from about 0.1% to about 0.3%, from about 0.3% to about 1%, or from about 1% to about 3% by weight of the pharmaceutical composition. In exemplary embodiments, the amount of the lubricant may be about 1% by weight of the pharmaceutical composition.

Coating

The pharmaceutical composition can be coated with one or more enteric coatings, seal coatings, film coatings, barrier coatings, compress coatings, fast disintegrating coatings, or enzyme degradable coatings.

In some cases, the formulation disclosed herein is coated with a coating material, e.g., a sealant. In some embodiments, the coating material is water soluble. In some embodiments, the coating material comprises a polymer, plasticizer, a pigment, or any combination thereof. In some embodiments, the coating material is a form of a film coating, e.g., a glossy film, a pH independent film coating, an aqueous film coating, a dry powder film coating (e.g., complete dry powder film coating), or any combination thereof. In some embodiments, the coating material is highly adhesive. In some embodiments, the coating material provides low level of water permeation. In some embodiments, the coating material provides oxygen barrier protection. In some embodiments, the coating material allows immediate disintegration for fast release of drug actives. In some embodiments, the coating material is pigmented, clear, or white. In some embodiments, the coating material is clear. Exemplary coating materials include, without limitation, polyvinyl alcohol (PVA), cellulose acetate phthalate (CAP), polyvinyl acetate phthalate (PVAP), methacrylic acid copolymers, cellulose acetate trimellitate (CAT), hydroxypropyl methylcellulose phthalate (HPMCP), hydroxypropyl methylcellulose (HPMC), hydroxy propyl methyl cellulose acetate succinate (hypromellose acetate succinate), shellac, sodium alginate, and zein. In some embodiments, the coating material comprises or is PVA. In some embodiments, the coating material comprises or is HPMC. An exemplary PVA-based coating material includes Opadry II. In some instances, the coating material is about 1, 2, 3, 4, 5, 6, 7, 8, 9, or 10% of the weight of the formulation. In some instances, the coating material represent between about 1% and about 15% of the total weight of each first particulate, including, but not limited to, between about 5% and about 10%, between about 6% and about 10%, between about 7% and about 10%, between about 8% and about 10%, or between about 9% and about 10%. In some instances, the coating material is greater than about 2%, greater than about 3%, greater than about 4%, greater than about 5%, greater than about 6%, greater than about 7%, greater than about 8%, greater than about 9%, or greater than about 10% of the weight of the formulation. In some instances, the coating material is less than about 2%, less than about 3%, less than about 4%, less than about 5%, less than about 6%, less than about 7%, less than about 8%, less than about 9%, or less than about 10% of the weight of the formulation.

Multiple coatings can be applied for desired performance. Further, the dosage form can be designed for immediate release, pulsatile release, controlled release, extended release, delayed release, targeted release, synchronized release, or targeted delayed release. For release/absorption control, solid carriers can be made of various component types and levels or thicknesses of coats, with or without an active ingredient. Such diverse solid carriers can be blended in a dosage form to achieve a desired performance. The definitions of these terms are known to those skilled in the art. In addition, the dosage form release profile can be affected by a polymeric matrix composition, a coated matrix composition, a multiparticulate composition, a coated multiparticulate composition, an ion-exchange resin-based composition, an osmosis-based composition, or a biodegradable polymeric composition. Without wishing to be bound by theory, it is believed that the release may be effected through favorable diffusion, dissolution, erosion, ion-exchange, osmosis or combinations thereof.

Dosage forms of the invention can further be coated with, for example, a seal coating, an enteric coating, an extended release coating, or a targeted delayed release coating. These various coatings are known in the art, but for clarity, the following brief descriptions are provided: seal coating, or coating with isolation layers: Thin layers of up to 20 microns in thickness can be applied for variety of reasons, including for particle porosity reduction, to reduce dust, for chemical protection, to mask taste, to reduce odor, to minimize gastrointestinal irritation, etc. The isolating effect is proportional to the thickness of the coating. Water soluble cellulose ethers are preferred for this application. HPMC and ethyl cellulose in combination, or Eudragit E100, may be particularly suitable. In exemplary embodiments, the coating may be OPADRY® Y-1-7000, a coating ready mix from Colorcon. Opadry Y-1-7000 contains hypromellose 5 cP, titanium dioxide and macrogol/PEG 400. Traditional enteric coating materials listed elsewhere can also be applied to form an isolating layer.

Optionally, the sustained-release matrix multiparticulate systems, tablets, or capsules can be coated with a sustained release coating such as the sustained release coatings described herein. Such coatings preferably include a sufficient amount of hydrophobic and/or hydrophilic sustained-release material to obtain a weight gain level from about 2 to about 25 percent, although the overcoat may be greater depending upon, e.g., the desired release rate. In certain embodiments, a sustained release coating is applied to the sustained release spheroids, granules, or matrix multiparticulates. In such embodiments, the sustained-release coating may include a water insoluble material such as (a) a wax, either alone or in admixture with a fatty alcohol; or (b) shellac or zein. The coating is preferably derived from an aqueous dispersion of the hydrophobic sustained release material.

In other preferred embodiments of the present invention, the sustained release material comprising the sustained-release coating is a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art as fully polymerized copolymers of acrylic and methacrylic acid esters with a low content of quaternary ammonium groups. In order to obtain a desirable dissolution profile, it may be necessary to incorporate two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit® from Rohm GMBH and Co. Kg Darmstadt, Germany. There are several different types of Eudragit®. For example, Eudragit E is an example of a methacrylic acid copolymer which swells and dissolves in acidic media. Eudragit L is a methacrylic acid copolymer which does not swell at about pH<5.7 and is soluble at about pH>6. Eudragit S does not swell at about pH<6.5 and is soluble at about pH>7. Eudragit RL and Eudragit RS are water swellable, and the amount of water absorbed by these polymers is pH-dependent; however, dosage forms coated with Eudragit RL and RS are pH-independent.

In certain preferred embodiments, the acrylic coating comprises a mixture of two acrylic resin lacquers commercially available under the Tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Methyl citrate is an especially preferred plasticizer for the aqueous dispersions of ethyl cellulose of the present invention.

Extended release coatings are designed to effect delivery over an extended period of time. The extended release coating is a pH-independent coating formed of, for example, ethyl cellulose, hydroxypropyl cellulose, methylcellulose, hydroxymethyl cellulose, hydroxyethyl cellulose, acrylic esters, or sodium carboxymethyl cellulose. Various extended release dosage forms can be readily designed by one skilled in art to achieve delivery to both the small and large intestines, to only the small intestine, or to only the large intestine, depending upon the choice of coating materials and/or coating thickness.

Enteric coatings are mixtures of pharmaceutically acceptable excipients which are applied to, combined with, mixed with or otherwise added to the carrier or composition. The coating may be applied to a compressed or molded or extruded tablet, a gelatin capsule, and/or pellets, beads, granules or particles of the carrier or composition. The coating may be applied through an aqueous dispersion or after dissolving in appropriate solvent.

In certain embodiments, the pharmaceutical composition, upon oral administration to a human or non-human patient in need thereof, provides controlled release for at least about 1, 2, 3, 4, 5, 6, 7, 8, 9, 10, 11, 12, 14, 16, 18, 20, 24, 36, 48, 72, 96, 120, 144, or 168 hours.

The term "sustained release" refers release of a drug from its dosage form (e.g., tablet) at such a rate that its blood levels are maintained within the therapeutic range (i.e., at or above minimum effective concentration (MEC)) but below toxic levels over an extended period of time (e.g., about 1, 2, 3, 4, 5, 6, 7, 8, 9, 10, 11, 12, 14, 16, 18, 20, 22, 24, 36, 48, 72, 96, 120, 144, or 168 hours or greater). The term "sustained release" may be used interchangeably with "slow-release," "controlled release," or "extended release." The sustained release property of a dosage form is typically measured by an in vitro dissolution method and confirmed by an in vivo blood concentration-time profile (i.e., a pharmacokinetic profile).

In certain embodiments, the pharmaceutical compositions of the present invention release about 90% to 100% of their pharmaceutically active agents in a linear or near linear fashion for at least about 1, 2, 3, 4, 5, 6, 7, 8, 9, 10, 11, 12, 13, 14, 15, 16, 17, 18, 19, 20, 21, 22, 23, 24, 36, 48, 72, 96, 120, 144, or 168 hours in an in vitro dissolution analysis.

Delayed release generally refers to the delivery so that the release can be accomplished at some generally predictable location in the lower intestinal tract more distal to that which would have been accomplished if there had been no delayed release alterations. The preferred method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present invention to achieve delivery to the lower gastrointestinal tract. Polymers for use in the present invention are anionic carboxylic polymers.

In exemplary embodiments, the coating may comprise shellac, also called purified lac, a refined product obtained from the, resinous secretion of an insect. This coating dissolves in media of pH>7.

Colorants, detackifiers, surfactants, antifoaming agents, lubricants, stabilizers such as hydroxy propyl cellulose, acid/base may be added to the coatings besides plasticizers to solubilize or disperse the coating material, and to improve coating performance and the coated product.

Pharmaceutical Dosage Forms

The compositions of the present invention can be processed by agglomeration, air suspension chilling, air suspension drying, balling, coacervation, coating, comminution, compression, cryopelletization, encapsulation, extrusion, wet granulation, dry granulation, homogenization, inclusion complexation, lyophilization, melting, microencapsulation, mixing, molding, pan coating, solvent dehydration, sonication, spheronization, spray chilling, spray congealing, spray drying, or other processes known in the art. The compositions can be provided in the form of a minicapsule, a capsule, a tablet, an implant, a troche, a lozenge (minitablet), a temporary or permanent suspension, an ovule, a suppository, a wafer, a chewable tablet, a quick or fast dissolving tablet, an effervescent tablet, a buccal or sublingual solid, a granule, a film, a sprinkle, a pellet, a bead, a pill, a powder, a triturate, a platelet, a strip or a sachet. Compositions can also be administered as a "dry syrup", where the finished dosage form is placed directly on the tongue and swallowed or followed with a drink or beverage. These forms are well known in the art and are packaged appropriately. The compositions can be formulated, for example, for oral, nasal, buccal, ocular, urethral, transmucosal, vaginal, topical or rectal delivery.

The pharmaceutical composition can be coated with one or more enteric coatings, seal coatings, film coatings, barrier coatings, compress coatings, fast disintegrating coatings, or enzyme degradable coatings. Multiple coatings can be applied for desired performance. Further, the dosage form can be designed for immediate release, pulsatile release, controlled release, extended release, delayed release, targeted release, synchronized release, or targeted delayed release. For release/absorption control, solid carriers can be made of various component types and levels or thicknesses of coats, with or without an active ingredient. Such diverse solid carriers can be blended in a dosage form to achieve a desired performance. The definitions of these terms are known to those skilled in the art. In addition, the dosage form release profile can be affected by a polymeric matrix composition, a coated matrix composition, a multiparticulate composition, a coated multiparticulate composition, an ion-exchange resin-based composition, an osmosis-based composition, or a biodegradable polymeric composition. Without wishing to be bound by theory, it is believed that the release may be effected through favorable diffusion, dissolution, erosion, ion-exchange, osmosis or combinations thereof.

In carrying out the method of the present invention, the compositions of the invention may be administered to mammalian species, such as dogs, cats, humans, etc. and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like.

The dose administered must be carefully adjusted according to age, weight and condition of the patient, as well as the route of administration, dosage form and regimen and the desired result.

The pharmaceutical compositions of the invention may be administered in the dosage forms in single or divided doses of one to four times daily. It may be advisable to start a patient on a low dose combination and work up gradually to a high dose combination.

Liquid formulations can be prepared by dissolving or suspending one or the combination of active substances in a conventional liquid vehicle acceptable for pharmaceutical administration so as to provide the desired dosage in one to four teaspoonful.

Dosage forms can be administered to the patient on a regimen of, for example, one, two, three, four, five, six, or other doses per day. The compositions of the invention as described herein may be administered, for example, for one day, two days, three days, four days, five days, six days, a week, two weeks, three weeks, four weeks, five weeks, six weeks, a month, two months, three months, four months, or more. The compositors of the invention as described herein may be administered, for example, for a prolonged period, that is, for as long as the potential for a disease or condition remains and/or the symptoms continue.

In order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

In formulating the compositions, the active substances, in the amounts described above, may be compounded according to accepted pharmaceutical practice with a physiologically acceptable vehicle, carrier, excipient, binder, preservative, stabilizer, flavor, etc., in the particular type of unit dosage form.

The liquid formulations useful herein may comprise a solvent, solution, suspension, microsuspension, nanosuspension, emulsion, microemulsion, gel or even a melt containing the active component or components. In some embodiments the nanoparticles, nanofibers, or nanofibrils may be in the form of, or within or on, granules, powders, suspensions, solutions, dissolvable films, mats, webs, tablets, or releasable forms particularly releasable dosage forms. Other particular useful forms are concentrates to which a diluting liquid is added prior to use. The product may also be sprayed onto the inner surface of a container to which a liquid is added later prior to use and the nanoparticles, nanofibers, or nanofibrils, are released into the liquid. Pharmaceutical compositions of the present invention can include nanoparticles, composite nanoparticles, nanosuspension, or nanocapsules of the present invention.

The composition may also include various antioxidants to retard oxidation of one or more active ingredient or nanoparticles, composite nanoparticles, nanosuspension, or nanocapsules. The prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In order to increase the effectiveness of a treatment with the nanoparticles, nanogels, composite nanoparticles, nanosuspension, or nanocapsules of the present invention, it may be desirable to combine these nanoparticles, composite nanoparticles, or nanocapsules with other therapies effective in the treatment of a particular disease or condition.

The formulations as described above may be administered for a prolonged period, that is, for as long as the potential for a disease or condition remains or the symptoms continue.

In certain such embodiments of the invention the formulation has a hardness or cracking force of at least about 110 N, preferably of at least about 120 N, at least about 130 N or at least about 140 N, more preferably of at least about 150 N, at least about 160 N or at least about 170 N, most preferably of at least about 180 N, at least about 190 N, at least about 200 N, at least about 210 N, at least about 220 N, at least about 230 N, at least about 240 N, or at least about 250 N.

Packaging/Treatment Kits

The present invention relates to a kit for conveniently and effectively carrying out the methods in accordance with the present invention. Such a kit may include a number of unit dosages. Such kits can include a means for containing the dosages oriented in the order of their intended use. An example of a means for containing the dosages in the order of their intended uses is a card. An example of such a kit is a "blister pack". Blister packs are well known in the packaging industry and are widely used for packaging pharmaceutical unit dosage forms. If desired, the blister can be in the form of a childproof blister, i.e., a blister that is difficult for a child to open, yet can be readily opened by an adult. If desired, a memory aid can be provided, for example in the form of numbers, letters, or other markings or with a calendar feature and/or calendar insert, designating the days and the sections of a day in the treatment schedule in which the dosages can be administered, such as an AM dose is packaged with a "mid day" and a PM dose; or an AM dose is packaged with a PM dose. Alternatively, placebo dosages, or vitamin or dietary supplements, either in a form similar to or distinct from the pharmaceutical active dosages, can be included.

As discussed herein, the products of manufacture of the invention can comprise the packaging of the therapeutic drug combinations of the invention, alone or in combination, as "blister packages" or as a plurality of packettes, including as lidded blister packages, lidded blister or blister card or packets, or a shrink wrap.

Other means for containing said unit dosages can include bottles and vials, wherein the bottle or vial comprises a memory aid, such as a printed label for administering said unit dosage or dosages. The label can also contain removable reminder stickers for placement on a calendar or dayminder to further help the patient to remember when to take a dosage or when a dosage has been taken.

Administration

The pharmaceutical compositions may be optimized for particular types of delivery. For example, pharmaceutical compositions for oral delivery are formulated using pharmaceutically acceptable carriers that are well known in the art. The carriers enable the agents in the composition to be formulated, for example, as a tablet, pill, capsule, solution, suspension, sustained release formulation; powder, liquid or gel for oral ingestion by the subject.

The liquid or solid compositions may contain suitable pharmaceutically acceptable excipients as set out above. Preferably the compositions are administered by the oral, intranasal or respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices that deliver the formulation in an appropriate manner.

Alternatively, the composition may be applied intermittently, or in a pulsed manner. Accordingly, an alternative embodiment of the invention is to apply the composition on an intermittent or pulsed dosage schedule. For example, the composition of the invention may be used for two or more days, stopped, then restarted again at a time from between 2 weeks to 3 months later, and at even more long-spaced intervals.

Dosages of the pharmaceutical composition of the invention are for example, 0.5 mg, 1.0 mg, 2.0 mg, 5.0 mg, 10 mg, 20 mg, 30 mg, 40 mg, 50 mg, 60 mg, 70 mg, 80 mg, 90 mg, 100 mg, 125 mg, 150 mg, 200 mg, 250 mg, 300 mg, 350 mg, 400 mg, 500 mg, 600 mg, and can be administered, for example, once daily, twice daily, three times daily, four times daily.

The treatments may include various "unit doses." Unit dose is defined as containing a predetermined-quantity of the therapeutic composition. The quantity to be administered, and the particular route and formulation, are within the skill of those in the clinical arts. A unit dose need not be administered as a single injection but may comprise continuous infusion over a set period of time. Alternatively, the amount specified may be the amount administered as the average daily, average weekly, or average monthly dose.

Hardness

In certain embodiments, the present invention is directed to a solid oral extended release pharmaceutical dosage form comprising an extended release matrix formulation, the extended release matrix formulation comprising a composition comprising:
  (1) at least one polyethylene oxide having, based on rheological measurements, an approximate molecular weight selected from the group consisting of at least about 1,000,000; at least about 2,000,000; at least about 3,000,000; at least about 4,000,000; at least about 5,000,000; at least about 6,000,000; at least about 6,000,000; at least about 7,000,000; and at least about 8,000,000; and
  (2) at least one active agent; and
wherein the extended release matrix formulation when subjected to an indentation test has a "hardness" of at least about 200 N.

In certain such embodiments of the invention the extended release matrix formulation has a hardness or cracking force of at least about 110 N, preferably of at least about 120 N, at least about 130 N or at least about 140 N, more preferably of at least about 150 N, at least about 160 N or at least about 170 N, most preferably of at least about 180 N, at least about 190 N, at least about 200 N, at least about 210 N, at least about 220 N, at least about 230 N, at least about 240 N, or at least about 250 N.

The invention will be illustrated in more detail with reference to the following Examples, but it should be understood that the present invention is not deemed to be limited thereto.

EXAMPLES

Example 1

Ketamine Sustained-Release Tablets 60 mg Formulation

| Excipients | mg/tablet | % (w/w) |
| --- | --- | --- |
| Ketamine HCl | 69.20 | 16.80 |
| Polyethylene Oxide | 326.80 | 79.32 |
| Magnesium Stearate | 4.00 | 0.97 |
| Opadry White Y-1-7000 (Coating) | 12.00 | 2.91 |
| Total | 412.00 | 100.00 |

Manufacturing Steps:
1. Mix ketamine HCl with polyethylene oxide in a suitable mixer until uniformed.
2. Blend magnesium stearate into the above dry powder mixture.
3. Compress the final powder blend into tablets with aim tablet mass of 400 mg and aim tablet hardness of 210 N.
4. Perform initial coating to protect tablets from damage in next step of tablets curing.
5. Cure tablets at the temperature range of 70° C. to 75° C. to achieve desired firmness.
6. Continue to coat tablets from above step to gain sufficient weight.

Example 2

Study ZPS-603 (Study 603) was a hybrid study design with 4 cohorts and multiple study objectives. The objectives of Cohorts 1, 2 and 3 were to evaluate the safety, pharmacokinetics (PK) and pharmacodynamics (PD) of an extended release ketamine oral formulation in healthy volunteers after single dose and multiple doses. The design was a double-blind, placebo-controlled single and multiple ascending dose study in healthy volunteers. Doses were 60 mg, 120 mg and 240 mg for Cohorts 1, 2 and 3 respectively. Each dose level was initially given as a single dose, then one week later as 5 doses given at 12 hour intervals. Endpoints included safety, tolerability, ketamine and norketamine PK, and PD (suicidality assessments, and dissociative symptom rating scale scores).

The objective of Cohort 4 was to evaluate efficacy, safety, PK and PD of an extended release ketamine oral formulation in patients with treatment-resistant depression and/or treatment-resistant anxiety (TRD/TRA). Patients were selected based on prior demonstrated mood response to subcutaneous ketamine, and clinically significant scores on the Montgomery Asberg Depression Rating Scale (MADRS; Montgomery 1979) and/or the Hamilton Anxiety Scale (HAMA; Hamilton 1959). The design was an open label multiple ascending dose study. The initial dose was 60 mg, and could be escalated by an additional 60 mg 12 hourly, based on assessment of mood symptoms, to a maximum dose of 240 mg, with a total of 7 doses given 12 hourly between 0 and 72 hours. Endpoints included safety, tolerability, ketamine and norketamine PK, and PD (mood ratings including the Fear Questionnaire (FQ; Marks 1979), HAMA and MADRS, and dissociative symptom rating scale scores).

A protocol amendment added a further objective to Cohort 4, namely to evaluate the safety and efficacy of up to 3 months dosing of the extended release ketamine oral formulation in patients with TRD/TRA, who responded to treatment in the initial 96 hour ascending dose phase of ZPS-603, in an open-label extension (OLE) treatment phase. Endpoints for the OLE were similar to those of the initial 96 hour ascending dose phase of ZPS-603.

Results, Cohorts 1-3:

Demographics: Mean (SD) parameters for Cohort 1-3 participants are shown in Table 1. One subject in Cohort 2 (#16) withdrew from the study between single and multiple dosing, for reasons unrelated to safety/tolerability.

TABLE 1

Demographic parameter

|  | Cohort 1 | Cohort 2 | Cohort 3 |
|---|---|---|---|
| Ketamine dose | 60 mg | 120 mg | 240 mg |
| N ketamine/placebo | 6/2 | 6/2 | 6/2 |
| Dropouts | 0 | 1 | 0 |
| Age (years) | 27 ± 10 | 23 ± 3 | 21 ± 1 |
| Number of Males/Females | 6/2 | 7/1 | 5/3 |
| Weight (kg) | 83.8 ± 10.2 | 74.9 ± 9.7 | 68.9 ± 6.7 |
| Height (cm) | 1.80 ± 0.09 | 1.76 ± 0.07 | 1.73 ± 0.07 |
| BMI (kg/m$^2$) | 25.9 ± 1.5 | 24.2 ± 2.1 | 23.1 ± 1.3 |

Safety: There were no changes of clinical significance in vital signs, ECGs, safety laboratory tests or urinalyses in any subjects in Cohorts 1-3 during or after study completion.

Tolerability: Adverse events reported by study group are shown in Table 2. The only adverse event to show dose-related increases in frequency was dissociation, in subjects dosed with 240 mg.

| Adverse event | Cohort 1 (60 mg) | Cohort 2 (120 mg) | Cohort 3 (240 mg) | All cohorts (Placebo) |
|---|---|---|---|---|
| Vascular disorders | | | | |
| Syncope | 0 | 0 | 0 | 1 |
| Dizziness | 0 | 1 | 1 | 0 |
| Respiratory, thoracic and mediastinal disorders | | | | |
| Throat irritation | 1 | 0 | 0 | 0 |
| epistaxis | 1 | 0 | 0 | 0 |
| Psychiatric disorders | | | | |
| Restlessness | 1 | 0 | 0 | 0 |
| Dissociation | 0 | 0 | 11 | 2 |
| Nervous system disorders | | | | |
| Headache | 2 | 0 | 1 | 0 |
| Gastrointestinal disorders | | | | |
| Nausea | 0 | 0 | 1 | 0 |
| General disorders and administration site conditions | | | | |
| Swelling at catheter site | 0 | 0 | 0 | 1 |
| Total | 5 | 1 | 14 | 4 |

Pharmacodynamics:

CADSS: Mean CADS S scores over time are shown in FIG. 2. Minor increases were noted at 3 hours after single dosing in Cohorts 1 and 3 (FIG. 2A), and at 3-12 hours after the first dose in the multiple dose phase for Cohort 3 (FIG. 2B). (It should be noted that the maximum score on this scale is 84 points and that these are minimal changes compared with subcutaneous or IV ketamine dosing).

Suicidality Ratings: No participants reported suicidal ideation at any time in Cohorts 1-3, as assessed by the Columbia Suicide Severity Rating Scale.

Pharmacokinetics: FIG. 3 shows mean concentration-time profiles of ketamine and norketamine after single and multiple doses of 60, 120 and 240 mg. Concentrations of both analytes were relatively stable for 5-10 hours after dosing, consistent with the sustained release characteristics of the tablet. Norketamine concentrations were approximately 10-fold higher than ketamine concentrations in both plots, reflecting extensive first pass metabolism after oral dosing. For all 3 cohorts, ketamine and norketamine pharmacokinetic parameters appeared to follow first order kinetics, specifically AUC and $C_{max}$ were dose proportional after single and multiple doses of ketamine 60 mg, 120 mg and 240 mg extended release tablets (FIG. 4). There appeared to be evidence of autoinduction, in that the multiple dose $AUC_{0-12}$ values for both ketamine and norketamine were less than the single dose $AUC_{0-\infty}$, and the ratio of these decreased in a dose-related manner (see Table 3). The mechanism for induction appears to be via CYP2B6. Ketamine induces activity of CYP2B6 (Chen 2010), and is itself metabolized by this enzyme.

TABLE 3

| | Ketamine | | | | | |
|---|---|---|---|---|---|---|
| | AUC | | | Cmax | | |
| Dose | SD[1] (0-∞) | MD[2] (0-12) | Ratio[3] | SD[1] | MD[2] (0-12) | Ratio[3] |
| 60 mg | 79.24 | 74.18 | 0.94 | 9.71 | 11.91 | 1.23 |
| 120 mg | 196.92 | 133.11 | 0.68 | 16.40 | 20.66 | 1.26 |
| 240 mg | 384.58 | 217.41 | 0.57 | 37.98 | 41.57 | 1.09 |

TABLE 4

Single and multiple dose AUC and Cmax for ketamine (upper panel) and norketamine (lower panel), and ratios. MD/SD AUC ratios less than 1 are suggestive of autoinduction (bolded).

Norketamine

| Dose | AUC | | | Cmax | | |
|---|---|---|---|---|---|---|
| | SD[1] (0-∞) | MD[2] (0-12) | Ratio[3] | SD[1] | MD[2] (0-12) | Ratio[3] |
| 60 mg | 872.21 | 980.54 | 1.12 | 73.74 | 124.65 | 1.69 |
| 120 mg | 2133.09 | 1697.06 | 0.80 | 161.24 | 229.91 | 1.43 |
| 240 mg | 4079.19 | 3019.81 | 0.74 | 314.67 | 421.11 | 1.34 |

[1]Single Dose
[2]Multiple Dose
[3]Ratio = MD/SD.

Results, Cohort 4:

Demographics: Mean (SD) parameters for Cohort 4 participants are shown in Table 5.

TABLE 5

| Demographic parameter | Cohort 1 |
|---|---|
| Dropouts | 0 |
| Age (years) | 27 ± 4 |
| Number of Males/Females | 4/3 |
| Weight (kg) | 82.1 ± 22.3 |
| Height (cm) | 1.75 ± 0.07 |
| BMI (kg/m²) | 26.5 ± 5.6 |

Diagnoses: All 7 patients had current diagnoses of Social Anxiety Disorder. Five also had diagnoses of Major Depressive Disorder (MDD), and one had comorbid Generalized Anxiety Disorder. At screening, mean HAMA score was 22.9 (consistent with moderate severity) and mean FQ score was 48.4 (approximately 2-fold higher than the non-clinical population mean). Mean MADRS score in the 5 patients with MDD was 31.2 (consistent with moderate depression).

Dosing: On Day 1 all 7 patients were dosed with 1×60 mg tablets in the morning. All 7 patients received 2×60 mg tablets at 12 hours, and all 7 patients received 3×60 mg tablets at 24 hours. At 36 hours 2 patients received 3×60 mg tablets and 5 patients received 4×60 mg tablets. At 48 hours, 1 patient received 3×60 mg tablets and 6 patients received 4×60 mg tablets. At 56 and 72 hours all 7 patients received 4×60 mg tablets (see Table 6).

TABLE 6

| Patient ID | Day 1 (mg) | | Day 2 (mg) | | Day 3 (mg) | | Day 4 (mg) |
|---|---|---|---|---|---|---|---|
| | am | pm | am | pm | am | pm | am |
| 039-25 | 60 | 120 | 180 | 180 | 180 | 240 | 240 |
| 042-26 | 60 | 120 | 180 | 240 | 240 | 240 | 240 |
| 040-27 | 60 | 120 | 180 | 240 | 240 | 240 | 240 |
| 043-28 | 60 | 120 | 180 | 240 | 240 | 240 | 240 |
| 041-29 | 60 | 120 | 180 | 180 | 240 | 240 | 240 |
| 038-30 | 60 | 120 | 180 | 240 | 240 | 240 | 240 |
| 044-32 | 60 | 120 | 180 | 240 | 240 | 240 | 240 |

Safety: There were no changes of clinical significance in vital signs, ECGs, safety laboratory tests or urinalyses in any subjects in Cohort 4 during or after study completion.

Tolerability: Adverse events reported by Cohort 4 are shown in Table 7. Overall, single and multiple doses of the extended release ketamine tablets were well tolerated.

TABLE 7

Adverse Events (total no. AEs reported/subject n)

| | Cohort 4 |
|---|---|
| Feeling spaced out | 1/1 |
| Headache | 3/3 |
| Lightheadedness | 1/1 |

Pharmacodynamics:

CADSS: Mean CADSS scores over time are shown in FIG. 5A. Mean CADSS scores tended to decrease over time. This contrasts markedly from the change in CADS S scores after subcutaneous (SC) ketamine. FIG. 5B shows mean CADSS scores up to 3 hours after oral and SC dosing, in six of seven Cohort 4 participants with both sets of data. Overall, multiple dose oral ketamine was not associated with dissociative symptoms, as evaluated by the CADSS scale.

Figure 6A:
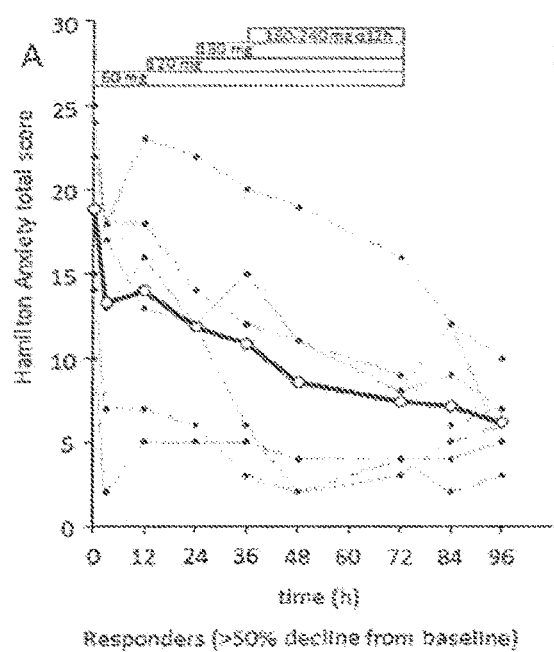
FIG. 6A is a chart showing the individual and mean Hamilton Anxiety Scale (HAMA) scores, Cohort 4 after dosing with extended release ketamine tablets.
Figure 6B:
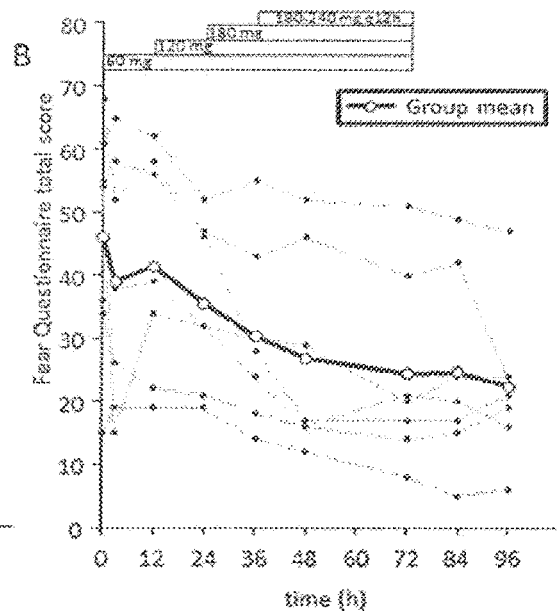
FIG. 6B is a chart showing the individual and mean Fear Questionnaire (FQ) scores, Cohort 4 after dosing with extended release ketamine tablets.
Figure 7:
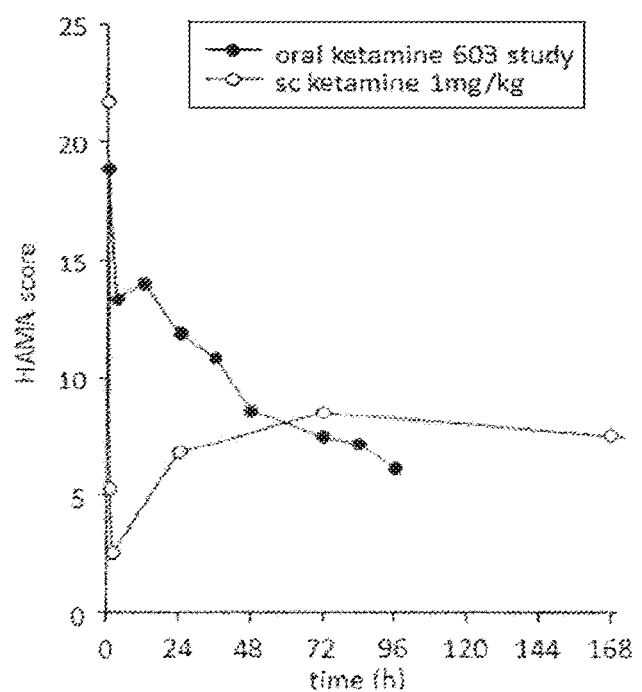
FIG. 7 is a chart showing comparison of mean HAMA scores after initial dosing with ketamine tablets (filled symbols) and subcutaneous ketamine (open symbols) in the 6 Cohort 4 participants with both sets of data.

Anxiety Rating Scales: HAMA and FQ: Individual and group mean HAMA and FQ scores by timepoint are shown in FIG. 6 (6A: HAMA; 6B: FQ) There was a consistent trend for both scores to decrease over time, most noticeably in patients with higher baseline scores. The trend for gradual improvement in anxiety contrasts markedly from the rapid reduction in anxiety scores after subcutaneous (SC) ketamine. FIG. 7 shows mean HAMA scores after oral and SC dosing, in six of seven Cohort 4 participants with both sets of data. All seven participants were assessed to be treatment responders (>50% reduction) based on changes in HAMA scores, and six of seven participants were responders based on changes in FQ scores.

MADRS: Individual and group mean MADRS scores by timepoint are shown in FIG. 8. There was a consistent trend for scores to decrease over time, most noticeably in patients with higher baseline scores. All seven participants were assessed to be treatment responders (>50% reduction) based on change in MADRS scores. Subject 042-026 reported worsening symptoms of depression at 48 and 72 h, without changes in ratings of anxiety. After discussion with clinic staff he reported that these were related to feelings of sadness at his experience of being excluded from group activities, rather than substantial and persistent changes in mood suggestive of a relapse of major depression. Following this discussion his MADRS scores fell again.

Figure 9A:
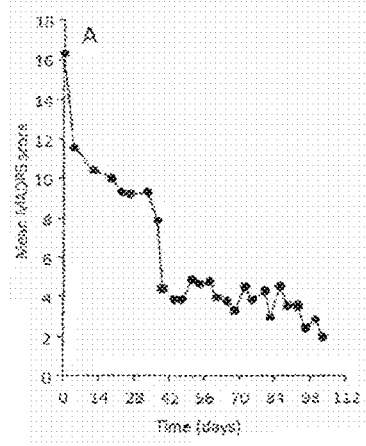
FIG. 9A is a chart showing the smoothed mean depression (MADRS) scores in 3 patients in Cohort 4, who entered a subsequent 3 month open-label extension (OLE) phase.
Figure 9B:
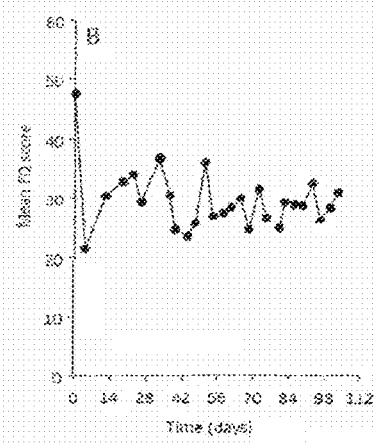
FIG. 9B is a chart showing anxiety (FQ) scores in the 3 patients in Cohort 4 who entered a subsequent 3 month open-label extension (OLE) phase.
Figure 9C:
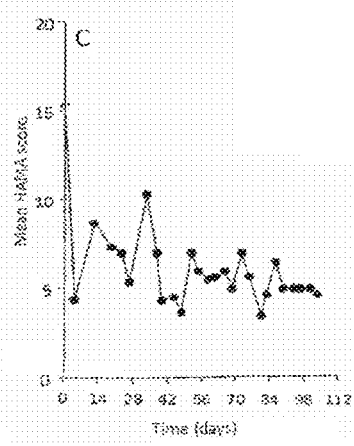
FIG. 9C is a chart showing anxiety (HAMA) scores in the 3 patients in Cohort 4 who entered a subsequent 3 month open-label extension (OLE) phase. All three patients reported improvements in mood ratings during this time. Mean depression ratings appeared to take 6 weeks for maximal improvement (FIG. 9A), whereas mean maximal anxiety scale improvement appeared to occur by week 2 (FIGS. 9B, 9C).

FIG. 9 shows smoothed mean depression (MADRS; 9A) and anxiety (FQ, HAMA; 9B and C) scores in 3 patients in Cohort 4, who entered a subsequent 3 month open-label extension (OLE) phase. All three patients reported improvements in mood ratings during this time. Mean depression ratings appeared to take 6 weeks for maximal improvement (FIG. 9A), whereas mean maximal anxiety scale improvement appeared to occur by week 2 (FIGS. 9B, 9C).

Pharmacokinetics: FIG. 10 shows mean concentration-time profiles of ketamine and norketamine over 96 hours in Cohort 4. Dose-related increases in both ketamine and norketamine plasma concentrations were noted out to 48 h, as patients continued to take higher doses. Norketamine concentrations were consistently higher than ketamine concentrations at all time points, reflecting extensive first pass metabolism. The data indicate a large inter-subject and intra-subject variation in the PK profiles.

Figure 11:
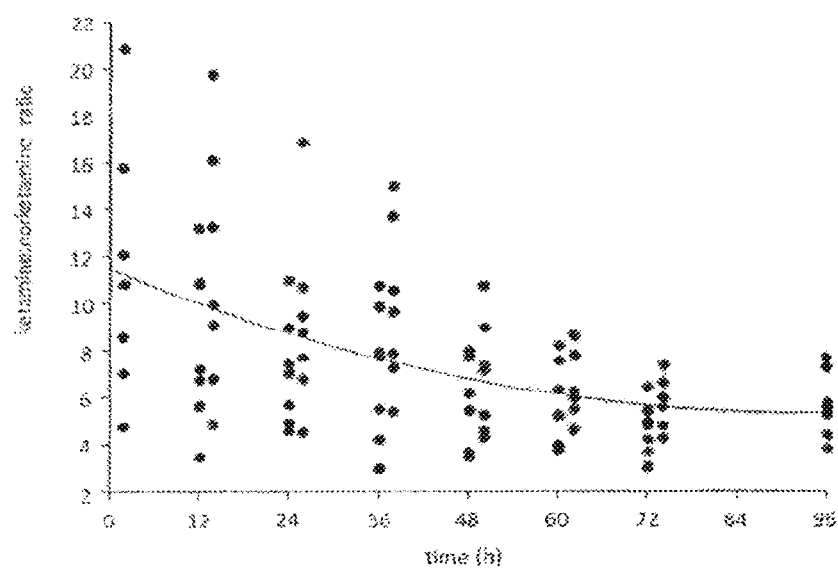
FIG. 11 is a chart showing changes in individual ketamine:norketamine ratios associated with 12 hourly dosing of extended release ketamine tablets, with a fitted regression line, Cohort 4.

To assess the impact of repeated dosing on enzyme induction, individual ketamine:norketamine (K:NK) ratios were calculated for each time point. These are plotted in FIG. 11. The mean ratio of K:NK was approximately 11 at 0 h, and progressively decreased to approximately 5 at 96 h. The correlation of K:NK ratios against time gave a coefficient of determination (r²) of 0.26. Data variability (expressed as % coefficient of variation) also decreased during multiple dosing, from 44% at 0 h to 23% at 96 h. These data are suggestive of increased first pass metabolism associated with repeat 12-hourly dosing, which appears to asymptote by 72 hours.

Example 3

Study 15/STH/86 was a hybrid study design with a preliminary acute ketamine dose response phase lasting 3-4 weeks, and a subsequent 3-month maintenance treatment phase. 24 patients with treatment-resistant anxiety disorders were dosed with 3 single ascending subcutaneous doses of ketamine (0.25, 0.5, 1 mg/kg), and 12 also received a dose of midazolam 0.01 mg/kg. 20 patients participated in the maintenance phase, where ketamine 1 mg/kg was administered 1-2× weekly for up to 14 weeks. Study assessments included mood ratings using the Fear Questionnaire (FQ; Marks and Mathews 1979) before and after each ketamine dose. The FQ scale includes a subscale that measures anxiety associated with Blood Injury (FQBI), a specific phobia.

Results: 25 patients participated in the acute dose-response phase and 20 patients participated in the maintenance phase.

Figure 12:
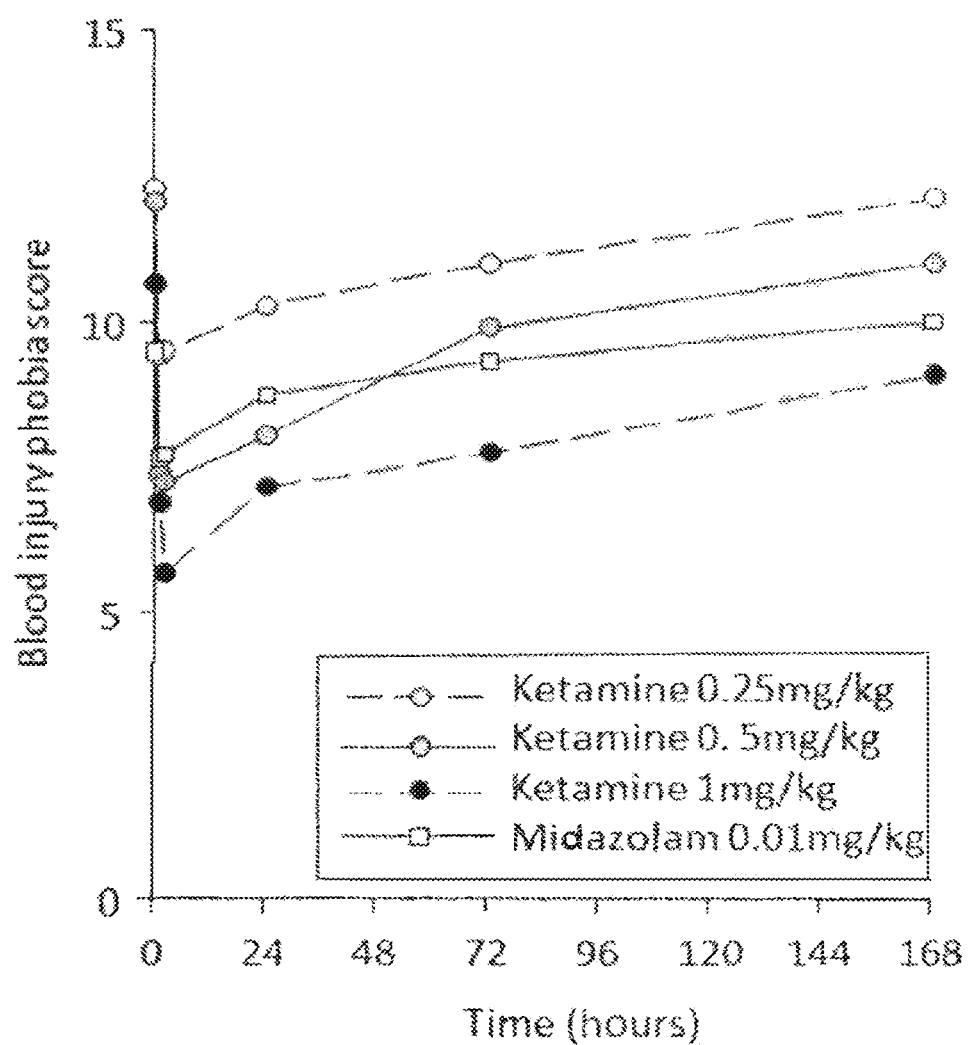
FIG. 12 is a graph showing the effects of ketamine dose on mean Fear Questionnaire Blood Injury (FQBI) scale scores, predose to 168 h post-dose

Anxiety Rating Scales—FQ acute dose-response: Baseline mean FQ Blood Injury (FQBI) scale score was 12.4. At 1 hour after ketamine dosing, there were rapid dose-related decreases in mean scores (FIG. 12). These scores gradually returned towards baseline over the next 168 h. The acute reduction and slow increase in scores were dose-related, with the higher ketamine doses having more durable effects compared with the lowest 0.25 mg/kg dose. Changes in FQBI scores after midazolam were similar to those of the 0.5 mg/kg ketamine dose profiles.

Figure 13A:
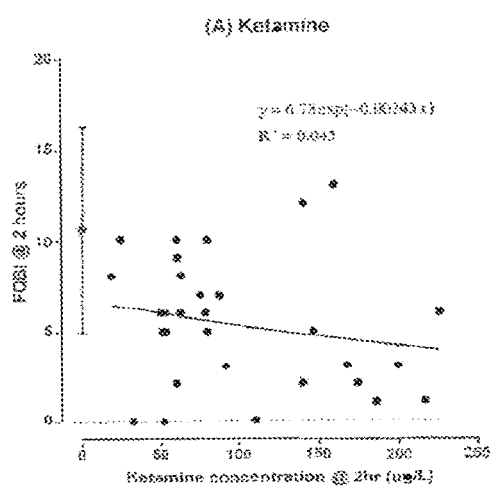
FIG. 13A is a graph showing changes from baseline in FQBI scores at 2 hours in relation to ketamine. The baseline FQBI scores are shown in red, with error bars representing the standard deviation (n=30).
Figure 13B:
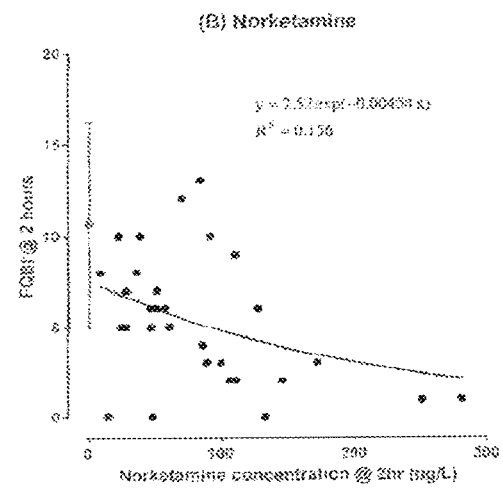
FIG. 13B is a graph showing changes from baseline in FQBI scores at 2 hours in relation to norketamine concentrations at 2 hours. The baseline FQBI scores are shown in red, with error bars representing the standard deviation (n=30).

Anxiety Rating Scales—FQ acute dose-response: Analysis of the relationship between ketamine and norketamine concentrations at 2 hours and FQBI scores is shown in FIGS. 13A and 13B respectively. Baseline FQBI scores are shown in red, with error bars representing the standard deviation. Higher concentrations were associated with lower FQBI scores, with a stronger correlation noted for norketamine compared with ketamine.

Figure 14:
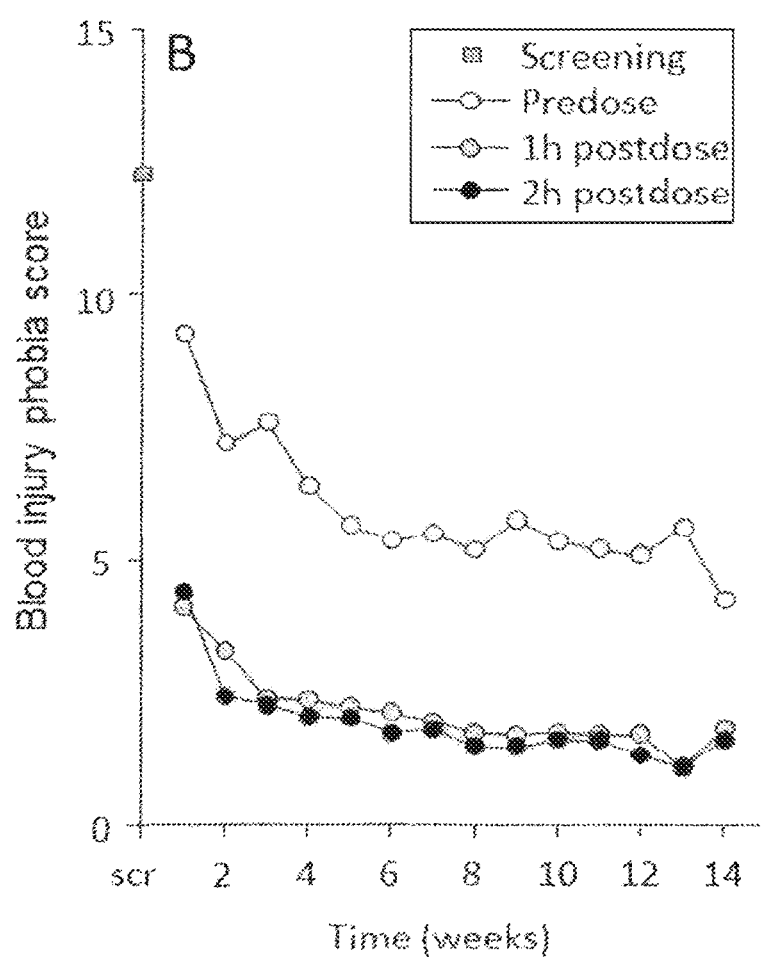
FIG. 14 is a graph showing the effects of maintenance ketamine treatment on mean FQBI scores over 14 weeks, predose and 1 and 2 h post-dose. The FQBI score prior to receiving any ketamine is also shown (grey symbol).

FQ maintenance treatment: Week 1 subscale predose scores were modestly lower compared with subscale scores at screening (i.e., prior to any ketamine treatment). Predose FQBI scores progressively decreased during maintenance treatment. After each dose, FQBI scores decreased by ~50% compared with predose scores by 1 hour, with no further improvement in score at 2 hours. See FIG. 14.

Example 4

The effect of the R-107 tablets (See Example 1) on avoidance and anxiety ratings in patients with a DSMS specific phobia, spider phobia is evaluated. In this study, participants with DSMS spider phobia are assessed initially via scores on a Fear of Spiders Questionnaire (FSQ; Symanski and O'Donohue 1995; minimum score 95) and performance in a Behavioural Avoidance Task (BAT; Garcia-Palacios et al 2002; maximum score 3). Patients with FSQ scores ≥95 demonstrate high phobic anxiety relating to spiders, and BAT scores ≤3 indicate high levels of phobic avoidance. After completing this testing, participants receive single doses of either R-107 tablets 120 mg or matching placebo tablets, under double-blind randomized conditions. Three hours later, patients again complete FSQ and BAT testing. Participants randomized to R-107 tablets report lower FSQ scores, and increased BAT scores compared with those randomized to placebo, indicating reduced phobic anxiety and avoidance.

While the invention has been described in detail and with reference to specific examples thereof, it will be apparent to one skilled in the art that various changes and modifications can be made therein without departing from the spirit and scope thereof

What is claimed is:

1. A solid, oral, extended release pharmaceutical tablet comprising:
    a core comprising:
    i) a therapeutically effective amount of an active agent selected from the group consisting of ketamine, norketamine, pharmaceutically acceptable salts thereof, and combinations thereof;
    ii) at least one high molecular weight polyethylene oxide (PEO) that is cured, wherein said high molecular weight PEO has an approximate molecular weight of from about 2 million to about 7 million, based upon rheological measurements, and is present in an amount of at least about 30% (by weight) of the core,
    wherein said tablet is crush resistant and has a breaking strength of at least about 200 N; and wherein said tablet comprises active agent at a concentration of at least about 12% by weight.

2. The tablet of claim 1 wherein the molecular weight of said high molecular weight PEO is selected from the group consisting of at least about 4,000,000; at least about 5,000,000; at least about 6,000,000; and at least about 7,000,000.

3. The tablet of claim 1 wherein said high molecular weight PEO comprises at least about 50% (by weight) of said core.

4. The tablet of claim 1 wherein the dosage amount of active agent is selected from the group consisting of about 30 mg, about 60 mg, about 120 mg, about 180 mg, and about 240 mg.

5. The tablet of claim 1 wherein the tablet is cured at a temperature of about 70° C. to about 75° C.

6. The tablet of claim 1 wherein the tablet is suitable for once weekly, twice weekly, three times weekly, once daily or twice-daily administration to a subject.

7. The tablet of claim 1 wherein the tablet has no or minimal dissociative side effects upon administration to a patient.

8. The tablet of claim 1 wherein after administration to a patient suffering from treatment-resistant depression or anxiety or phobia, the symptoms of said treatment-resistant depression or said anxiety or said phobia in said patient are measurably alleviated within about 1-3 or about 2 hours of oral administration of said ketamine to said patient.

9. The tablet of claim 1 wherein a single oral administration to a patient suffering from treatment-resistant depression or anxiety or phobia of said ketamine in doses between 30-180 mg is sufficient to alleviate the effects of said depression or said anxiety or said phobia for 3-7 days in said patient.

10. The tablet of claim 1 wherein the active agent is ketamine.

11. The tablet of claim 1 wherein said tablet provides a pharmacokinetic parameter of a ketamine $C_{max}$ between about 12 and about 42 ng/mL after administration of a single tablet to a patient.

12. The tablet of claim 1 wherein said tablet provides a pharmacokinetic parameter of a ketamine $AUC_{0-inf}$ between about 79 and about 385 ngh/mL after administration of a single tablet to a patient.

13. The tablet of claim 1 wherein said tablet provides a pharmacokinetic parameter of a norketamine $C_{max}$ between about 7 4 and about 315 ng/mL after administration of a single tablet to a patient.

14. The tablet of claim 1 wherein said tablet provides a pharmacokinetic parameter of a norketamine $AUC_{0-inf}$ between about 872 and about 4079 ngh/mL after administration of a single tablet to a patient.

15. A solid, oral, extended release pharmaceutical tablet comprising:
   a core comprising:
   i. a therapeutically effective amount of an active agent selected from the group consisting of ketamine, norketamine, pharmaceutically acceptable salts thereof, and combinations thereof;
   ii. at least one high molecular weight polyethylene oxide (PEO) that is cured, wherein said high molecular weight PEO has an approximate molecular weight of from about 2 million to about 7 million, based upon rheological measurements, and is present in an amount of at least 30% by weight of the core,
   wherein said tablet is crush resistant and has a breaking strength of at least 200 N; wherein said tablet comprises active agent at a concentration of at least about 12% by weight, and wherein the tablet is cured at a temperature of about 70° C. to about 75° C.

16. A process of preparing a solid, oral, extended release pharmaceutical tablet comprising the steps of:
   a) combining:
   i. at least one high molecular weight polyethylene oxide (PEO), wherein said high molecular weight PEO has an approximate molecular weight of from about 2 million to about 7 million, based upon rheological measurements; and
   ii. an active agent selected from the group consisting of ketamine, norketamine, pharmaceutically acceptable salts thereof, and combinations thereof, to form a composition;
   b) shaping the composition to form a tablet; and
   c) curing said tablet at a curing temperature of about 68° C. to about 80° C. for a time period of at least about 10 minutes,
   wherein said tablet comprises active agent at a concentration of at least about 12% by weight.

17. A solid, oral, extended release pharmaceutical tablet obtained by a process according to claim 16.

18. The tablet of claim 1 wherein said tablet comprises active agent at a concentration of at least about 12% to about 20% by weight.

19. The tablet of claim 15 wherein said tablet comprises active agent at a concentration of at least about 12% to about 20% by weight.

20. The process of claim 16 wherein said tablet comprises active agent at a concentration of at least about 12% to about 20% by weight.

21. A solid, oral, extended release pharmaceutical tablet obtained by a process according to claim 20.

* * * * *